(12) United States Patent
Hirata

(10) Patent No.: US 7,762,950 B2
(45) Date of Patent: Jul. 27, 2010

(54) ENDOSCOPE

(75) Inventor: Yasuo Hirata, Tokyo (JP)

(73) Assignee: Olympus Corporation (JP)

( * ) Notice: Subject to any disclaimer, the term of this patent is extended or adjusted under 35 U.S.C. 154(b) by 1287 days.

(21) Appl. No.: 11/231,687

(22) Filed: Sep. 21, 2005

(65) Prior Publication Data

US 2006/0058584 A1    Mar. 16, 2006

(51) Int. Cl.
*A61B 1/06* (2006.01)
(52) U.S. Cl. .................. 600/179; 600/129; 600/136; 600/178; 600/175; 439/226
(58) Field of Classification Search ................ 600/112, 600/129, 136, 172, 175, 178, 179; 362/572, 362/574; 439/226, 236, 242
See application file for complete search history.

(56) References Cited

U.S. PATENT DOCUMENTS

| 2003/0045147 | A1* | 3/2003 | Huang .................. 439/226 |
| 2004/0032751 | A1* | 2/2004 | Solovay et al. ........ 362/580 |
| 2005/0177027 | A1* | 8/2005 | Hirata .................. 600/179 |
| 2005/0182291 | A1* | 8/2005 | Hirata .................. 600/101 |
| 2006/0132786 | A1* | 6/2006 | Helbing ................ 356/446 |

FOREIGN PATENT DOCUMENTS

| JP | S53-43989 | | 4/1978 |
| JP | 60-088921 | | 5/1985 |
| JP | 61-047920 | | 3/1986 |
| JP | 06264625 | A * | 9/1994 |
| JP | 06267624 | A * | 9/1994 |
| JP | 06275348 | A * | 9/1994 |
| JP | H10-216085 | | 8/1998 |
| JP | H11-76151 | | 3/1999 |
| JP | 11-216113 | | 8/1999 |
| JP | 11-253398 | | 9/1999 |
| JP | 11-267099 | | 10/1999 |
| JP | 11-295620 | | 10/1999 |
| JP | 2001-351404 | | 12/2001 |
| JP | 2002-562 | | 1/2002 |

(Continued)

OTHER PUBLICATIONS

Japanese Patent Office Action dated Jan. 19, 2010 in corresponding Japanese Patent Application No. 2004-089177 (with English language translation).

(Continued)

*Primary Examiner*—John P Leubecker
*Assistant Examiner*—Samuel Candler
(74) *Attorney, Agent, or Firm*—Ostrolenk Faber LLP

(57) ABSTRACT

An endoscope includes an adaptor detachably mounted on a distal end of an insertion section; a mounting base provided in said adaptor; illumination section attached to the front of said mounting base; front electrode terminals provided at the front end of the mounting base and connected to the illumination section; rear electrode terminals provided at the back of the mounting base, connected to the front electrode terminals, and abutting electrode terminals provided at the distal end of the insertion section when the adaptor is mounted on the distal end of the insertion section; and insulating plates where the front and rear electrode terminals are provided in a manner such that they are exposed from the surface and coupling lines to couple the front and rear electrode terminals are embedded.

11 Claims, 34 Drawing Sheets

FOREIGN PATENT DOCUMENTS

| | | |
|---|---|---|
| JP | 2002-058633 | 2/2002 |
| JP | 2002-263057 | 9/2002 |
| JP | 2003-019107 | 1/2003 |
| JP | 2005-502083 | 1/2005 |
| WO | WO03/021329 | 3/2003 |

OTHER PUBLICATIONS

Office Action issued by Japanese Patent Office on Feb. 23, 2010 in connection with corresponding Japanese Patent Application No. 2004-166932 English translation of Japanese Office Action issued Feb. 23, 2010 submitted as a statement of relevancy of the prior art against instant application.

English translation of Japanese Office Action issued Feb. 23, 2010 submitted as a statement of relevancy of the prior art against instant application.

\* cited by examiner

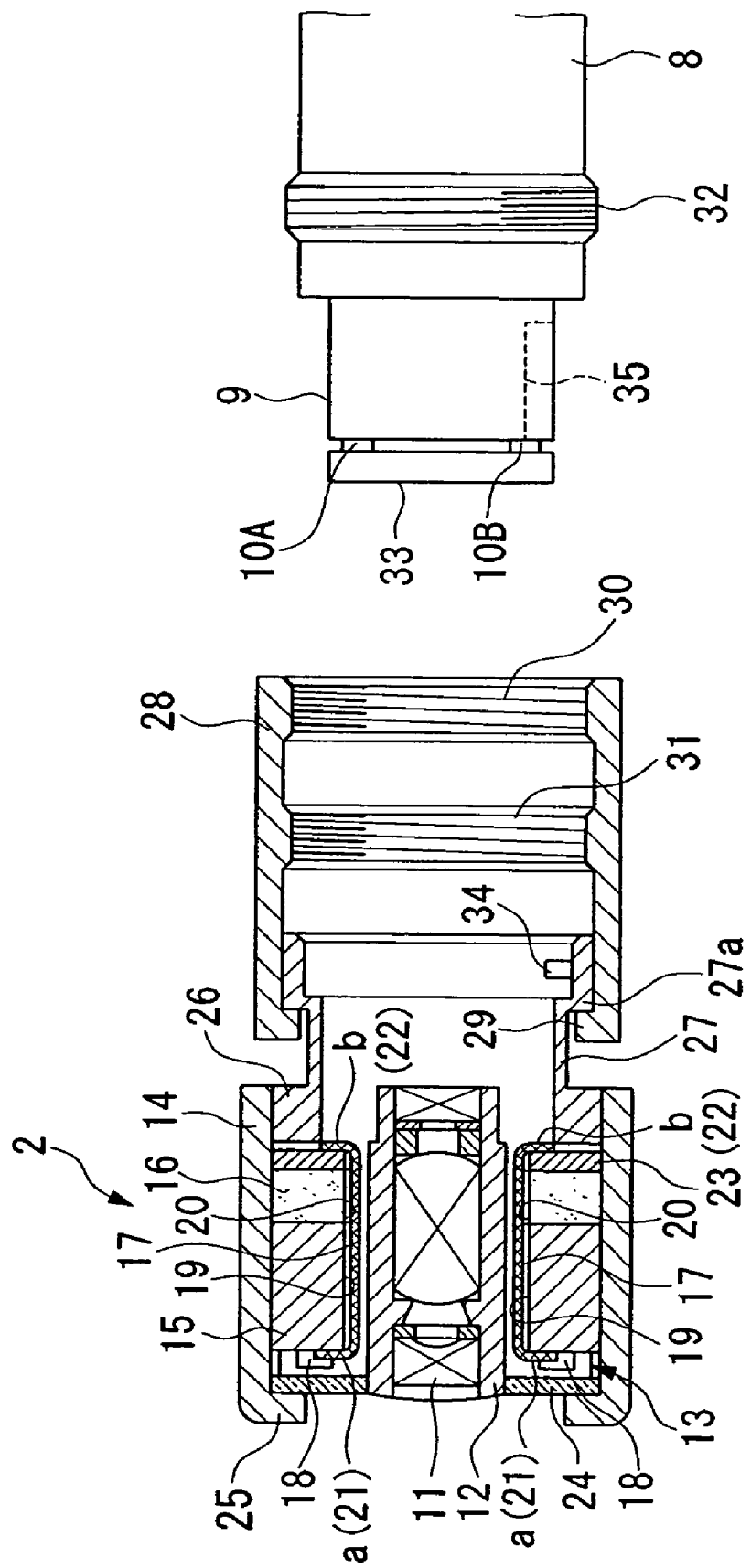

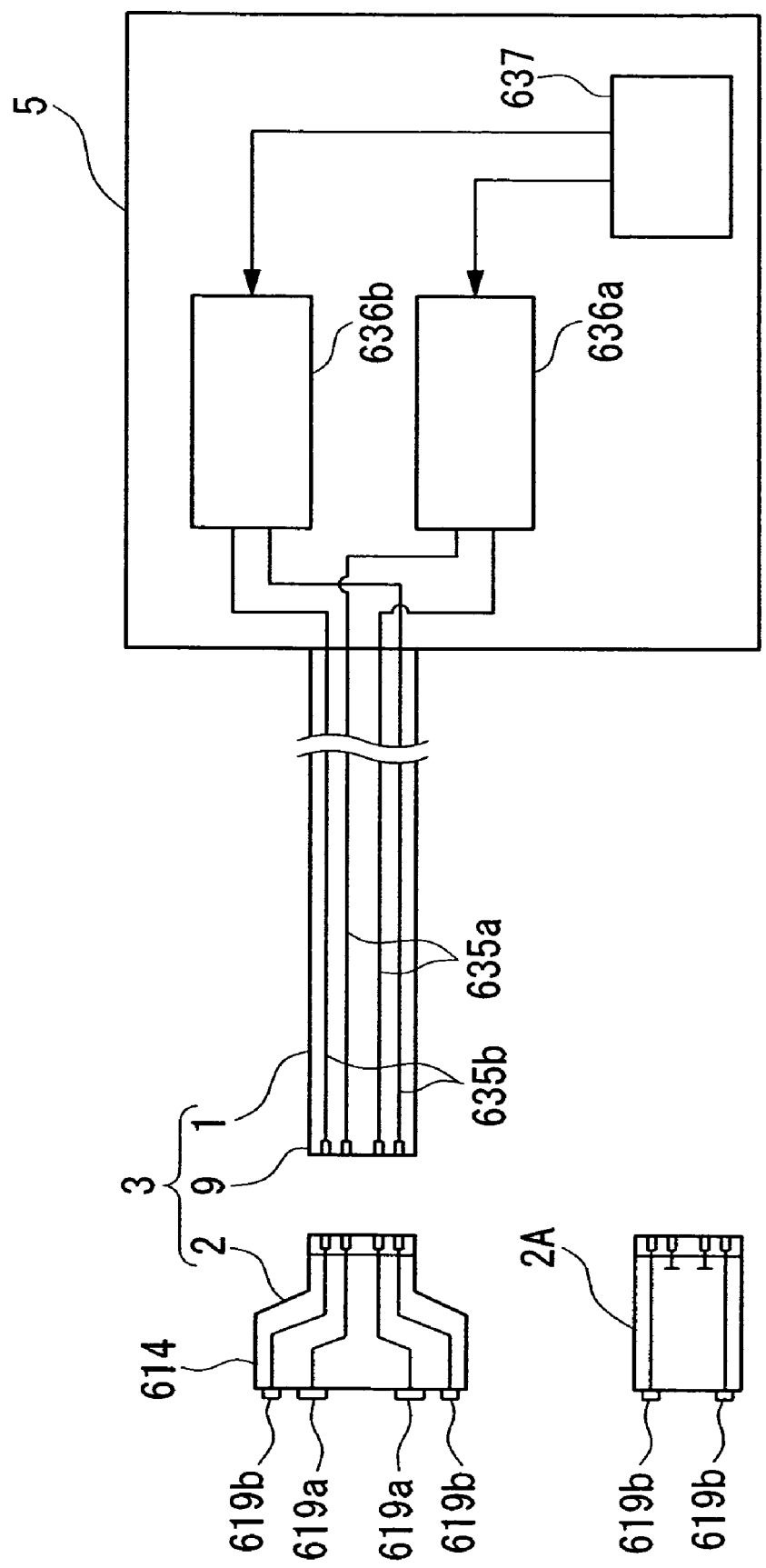

ENDOSCOPE

BACKGROUND OF THE INVENTION

1. Field of the Invention

The present invention relates to an endoscope provided with illumination section such as an LED at the insertion section that is inserted into an object to be examined.

2. Description of Related Art

An industrial and medical endoscope is provided at the insertion section that is inserted into a lumen with an observation or imaging optical system and illumination section for illuminating around an object to be examined within the lumen. The illumination section often uses an external light source to illuminate the object via an optical fiber. In recent years, light emitting diodes (hereafter referred to as LEDs) have been provided at the insertion section to illuminate around an object to be examined (reference is made, for example, to Japanese Unexamined Patent Application, First Publication No. H10-216085, Japanese Unexamined Patent Application, First Publication No. H11-76151, and Japanese Unexamined Patent Application, First Publication No. 2002-562).

In the endoscope described in the Japanese Unexamined Patent Application, First Publication No. H10-216085 and the Japanese Unexamined Patent Application, First Publication No. H11-76151, multiple LED package chips are integrally attached to the mounting base of an adaptor detachably mounted on the distal end of the insertion section body. An LED package chip is a package including an LED bare chip plus electrodes, a fluorescent layer, a sealing layer, and the like. Coupling connectors are provided at the rear end of the adaptor and at the distal end of the insertion section body. With the connectors coupled, the LEDs are powered from a power unit in the main device. The LED package chips are attached to the front of the mounting base and soldered to one end of wires that run through the mounting base in the axial direction of the adaptor. The other ends of the wires are soldered to the connector on the adaptor.

In the above endoscope, each LED package must be soldered, leading to poor assembly workability. Particularly, assembly is troublesome when a number of LED packages are mounted.

Then, in the endoscope described in the Japanese Unexamined Patent Application, First Publication No. 2002-562, wiring is printed on the front of an insulating mounting base made, for example, of glass epoxy, and LED package chips are mounted on the mounting base and connected to the printed wiring. Electrodes on the printed wiring and electrodes at the back of the mounting base are connected via wires. In this endoscope, LED package chips are soldered to the printed wiring on the mounting base before assembly. The electrodes on the printed wiring and the electrodes at the back of the mounting base are connected during assembly, by which the wires can be reduced in number. The electrodes at the front and back of the mounting base are connected by soldering to either end of the wires that run through the mounting base. The electrodes at the back of the mounting base abut and are connected to power terminals on the insertion section body.

SUMMARY OF THE INVENTION

The endoscope of the present invention includes an adaptor detachably mounted on the distal end of the insertion section; a mounting base provided in the adaptor; illumination section attached to the front of the mounting base; front electrode terminals provided at the front of the mounting base and connected to the illumination section; rear electrode terminals provided at the back of the mounting base, electrically connected to the front electrode terminals, and abutting electrode terminals provided at the distal end of the insertion section when the adaptor is mounted on the distal end of the insertion section; and insulating plates on which the front and rear electrode terminals are provided in such a manner that they are exposed from its surface and in which connection lines to connect the front and rear electrode terminals.

It is preferable in the endoscope of the present invention that the insulating plates be made of a flexible material.

It is preferable in the endoscope of the present invention that an elastic member that supports the rear electrode terminals be provided between the rear electrode terminals and the mounting base.

It is preferable in the endoscope of the present invention that the part of the insulating plate where the rear electrode terminal is provided be protrude and be elastically deformable.

It is preferable in the endoscope of the present invention that a sensor be provided on the insulating plate. It is further preferable that the sensor be a temperature sensor, a pressure sensor, a humidity sensor, or a gravity direction detection sensor.

The endoscope of the present invention includes an adaptor detachably mounted on a distal end of an insertion section, an illumination section attached to the adaptor, a first flexible insulating plate provided in the adaptor and mounted the illumination section, adaptor's side electrode terminals provided at the first flexible insulating plate, and main body side electrode terminals provided at a distal end of the insertion section.

It is preferable in the endoscope of the present invention that a second flexible insulating plate be further provided at the distal end of the insertion section; and the main body's side electrode terminals be provided at the second flexible insulating plate.

It is preferable in the endoscope of the present invention that the adaptor side electrode terminals be formed integrally with the first flexible insulating plate or projection members fixed on the surface of the first flexible insulating plate.

It is preferable in the endoscope of the present invention that power supply pads be provided on the surface of the first flexible insulating plate and power supply lines be connected to the power supply pads. Alternatively, it is preferable that the first flexible insulating plate be provided through-holes, that power supply pads be provided on the inner periphery of the through-holes, and that power supply lines be connected to the power supply pads.

It is preferable in the endoscope of the present invention that the main body side electrode terminals be integrally formed with the second flexible insulating plate or projection members fixed on the surface of the second flexible insulating plate.

It is preferable in the endoscope of the present invention that power supply pads be provided on the surface of the second flexible insulating plate and that power supply lines be connected to the power supply pads. Alternatively, it is preferable that the second flexible insulating plate be provided with through-holes, that power supply pads be provided on the inner periphery of the through-holes, and that power supply lines be connected to the power supply pads.

The endoscope of the present invention includes an insertion section to be inserted in a lumen of an object to be examined; multiple illumination LED elements provided at the distal end of the insertion section; and a mounting base integrally provided with the insertion section, wherein the multiple LED elements include multiple kinds of LED elements that are different in shape or size; the multiple LED elements being attached to the mounting base; and the front surface of some of the multiple LED elements being covered with a transmitting sealing member.

It is preferable in the endoscope of the present invention that among multiple LED elements, one kind of LED elements are arranged between adjacent kinds of LED elements that are different to the one kind of LED elements.

It is preferable in the endoscope of the present invention that the mounting base has a circular shape; one kind of LED elements among the multiple LED elements being arranged in a circle on the mounting base; and a different kind of LED elements to the one kind of LED elements being arranged in a circle circumferentially offset to the one kind of LED base chips.

It is preferable in the endoscope of the present invention that the transmitting sealing member be a fluorescent substance. It is preferable that the transmitting sealing member be partly changed in thickness according to the kind of the LED elements to cover with the transmitting sealing member. It is further preferable that the transmitting sealing member be partly changed in material properties according to the kind of the LED elements to cover with the transmitting sealing member.

It is preferable in the endoscope of the present invention that the transmitting sealing member be a cover lens. It is preferable that the transmitting sealing member be partly changed in optical properties according to the kind of the LED elements to cover with the transmitting sealing member.

It is preferable in the endoscope of the present invention that the mounting base consists of multiple base plates adhered together, each being provided with a different kind of LED elements.

It is preferable in the endoscope of the present invention that the mounting base be a flexible insulating plate.

It is preferable in the endoscope of the present invention that the insertion section has a mounting base supporting surface having a truncated cone shape and that the mounting base be attached to the mounting base supporting surface.

It is preferable in the endoscope of the present invention that the insertion section has a mounting base supporting surface having a cylindrical shape and that the mounting base be attached to the mounting base supporting surface.

It is preferable in the endoscope of the present invention that a reflecting surface be provided at the back of the mounting base.

It is preferable in the endoscope of the present invention that among multiple LED elements, the same kind of LED elements be connected by LED wires; and that the LED wires be connected to separate, individual electric current control circuits.

It is preferable in the endoscope of the present invention that among multiple LED elements, the same kind of LED elements be connected by LED wires; the LED wires be connected to a common electric current control circuit; and that electric current correction resistors be provided to any LED wires.

It is preferable in the endoscope of the present invention that an adaptor detachably mounted on the distal end of the insertion section be further provided; and that the multiple LED elements, mounting base, transmitting sealing member, LED wires, and electric current correction resistors be provided in the adaptor.

BRIEF DESCRIPTION OF THE DRAWINGS

FIG. 1 is a vertical cross-sectional view of the core showing first embodiment of the present invention.

FIGS. 18A to 18D are perspective views showing the structures of an adaptor's side insulating plates that comply with the insertion section's side structure shown in FIG. 18A.

FIG. 34 is a schematic LED wiring diagram showing twelfth embodiment.

DESCRIPTION OF THE PREFERRED EMBODIMENTS

Embodiments of the present invention are described hereafter with reference to the drawings. The same reference numbers are given to the same components throughout the embodiments and a duplicated explanation is omitted. In the embodiments, the front means the end where an adaptor objective lens is placed and the rear means the end where the insertion section is attached.

FIGS. 1 to 6 show first embodiment of the endoscope of the present invention.

Figure 2A:
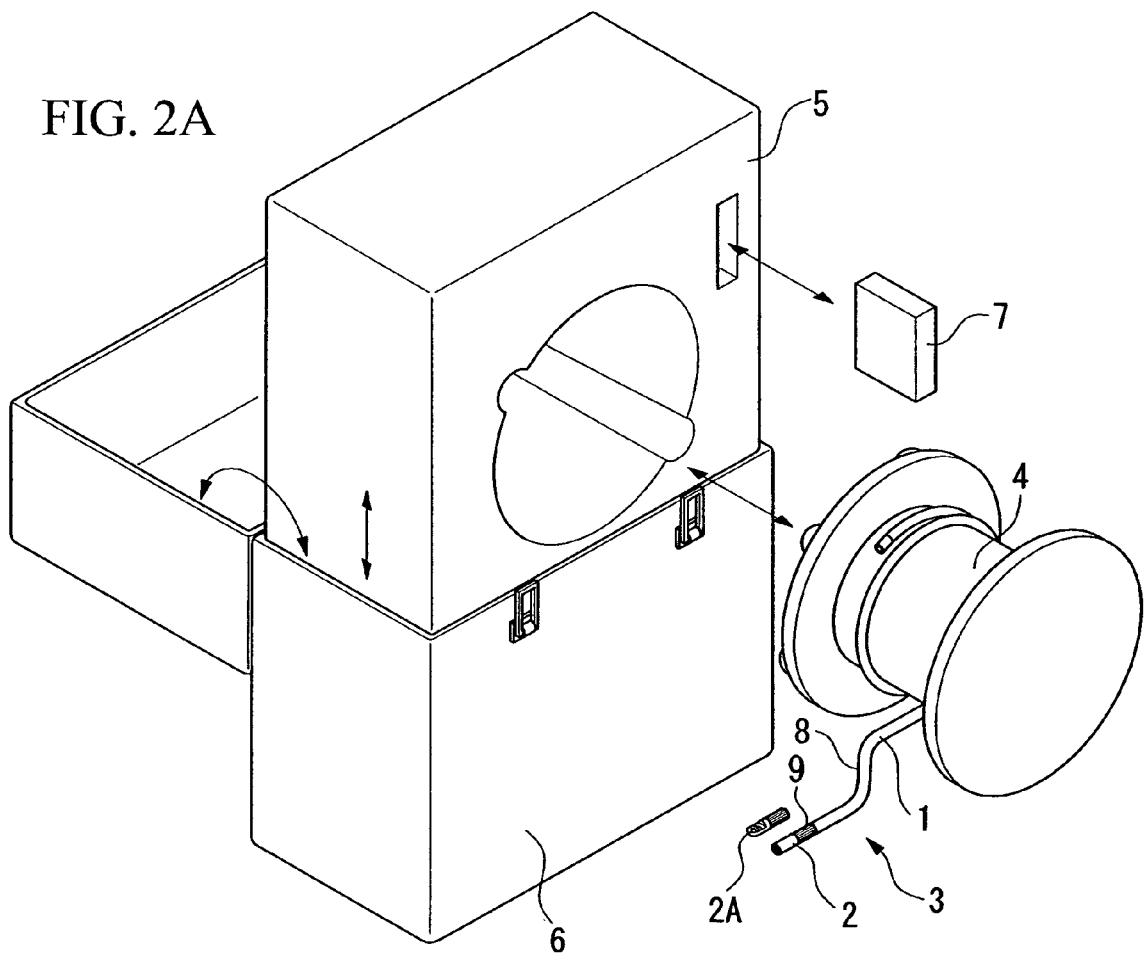
FIG. 2A is an exploded perspective view to schematically show the entire structure of the endoscope of first embodiment.
Figure 2B:
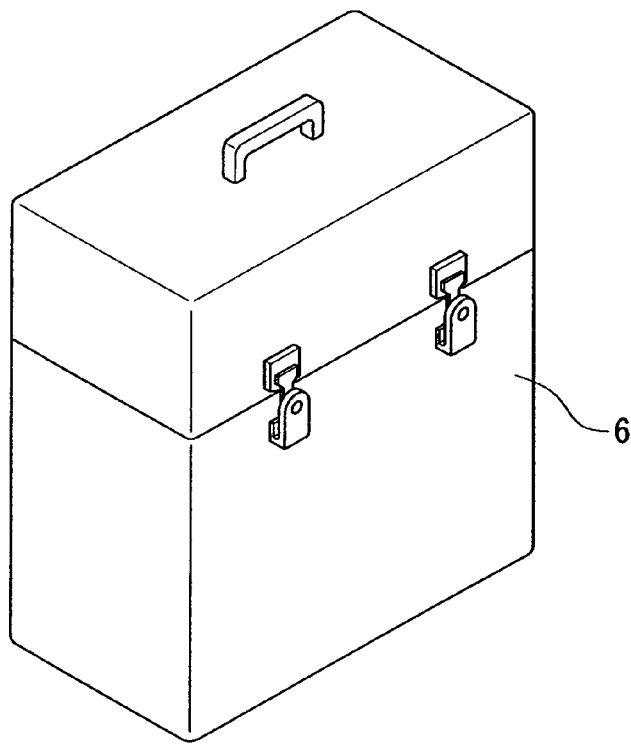
FIG. 2B is a perspective view of the endoscope of first embodiment after being assembled.

FIGS. 2A and 2B schematically show the entire structure of the endoscope of the present invention. As shown in FIGS. 2A and 2B, the endoscope includes an insertion section 3 having a lens adaptor 2 (adaptor) at the distal end of an elongated flexible tube 1, a take-up drum 4 that takes up the insertion section 3, and a device frame 5 that rotatably stores and holds the take-up part of the take-up drum 4. The endoscope further includes a storage case 6 that stores the device frame 5 together with the take-up drum 4 during transportation and an adaptor storage box 7 that stores a replacement lens adaptor 2A.

The insertion section 3 of the endoscope is provided with a CCD (not shown) as an imaging means. Image signals captured by the CCD are supplied to a signal processing circuit (not shown) provided in the take-up drum 4 via a signal line in the flexible tube 1. Image signals processed by the signal processing circuit are visualized and displayed on an image display means such as a liquid crystal panel (not shown) provided on, for example, the non-rotatable part on the side of the take-up drum 4. Besides the signal processing circuit, a main power circuit connected to a battery power (not shown), an operation actuator for bending/operating the distal end of the insertion section 3 in any direction (not shown), and the like are provided in the take-up drum 4.

The insertion section 3, which is to be inserted in an object, has the lens adaptor 2 disposed at the distal end of the flexible tube 1 as described above. Specifically, a bent part 8 that is operated by the aforementioned operation actuator is provided at the distal end of the flexible tube 1. The lens adaptor 2 is detachably connected to a coupling plug 9 provided on the distal end side of the bent part 8. In this embodiment, the insertion section body consists of the flexible tube 1, the bent part 8, the coupling plug 9, and the like. The coupling plug 9 is made of a hard material such as a metal. The CCD as described above and a pair of electrode terminals 10A and 10B protruding forward are provided on the distal end surface of the coupling plug 9. The electrode terminals 10A and 10B are connected to the main power circuit within the take-up drum 4 via lead lines (not shown) in the flexible tube 1 (see FIGS. 2A and 2B).

The lens adaptor 2 shown in FIG. 1 is a so-called straight view type. An objective lens group 11 that faces an object to be examined and forms an image of the object on the CCD in the coupling plug 9 is axially arranged in series in the lens adaptor 2. The objective lens group 11 is housed in a cylindrical lens holder 12 and further housed in a cylindrical adaptor housing 14 together with an LED illumination unit 13, described later.

The LED illumination unit 13 includes, as shown in FIGS. 1, 3, 4 and 5, a mounting base 15, a rubber elastic body 16, two insulting plates 17, and multiple LED bare chips (LED elements) 18. The mounting base 15 is made of a highly thermal conductive metal material such as aluminum. The rubber elastic body 16 is fixed on the rear surface of the mounting base 15. The insulating plates 17 each have a pair of metal electrodes a and b embedded on either end. The LED bare chips 18 are attached to the front surface of the mounting base 15.

The mounting base 15 and rubber elastic body 16 are bored discs having the same outer diameter. Their outer peripheries fit into the inner periphery of the adaptor housing 14 and are engaged therein. The inner periphery of the mounting base 15 and rubber elastic body 16 fit onto the outer periphery of the lens holder 12 and are fixed thereto. Wire guide grooves 19 and 20 are axially formed on the inner periphery of the mounting base 15 and rubber elastic body 16 at facing positions.

Figure 3:
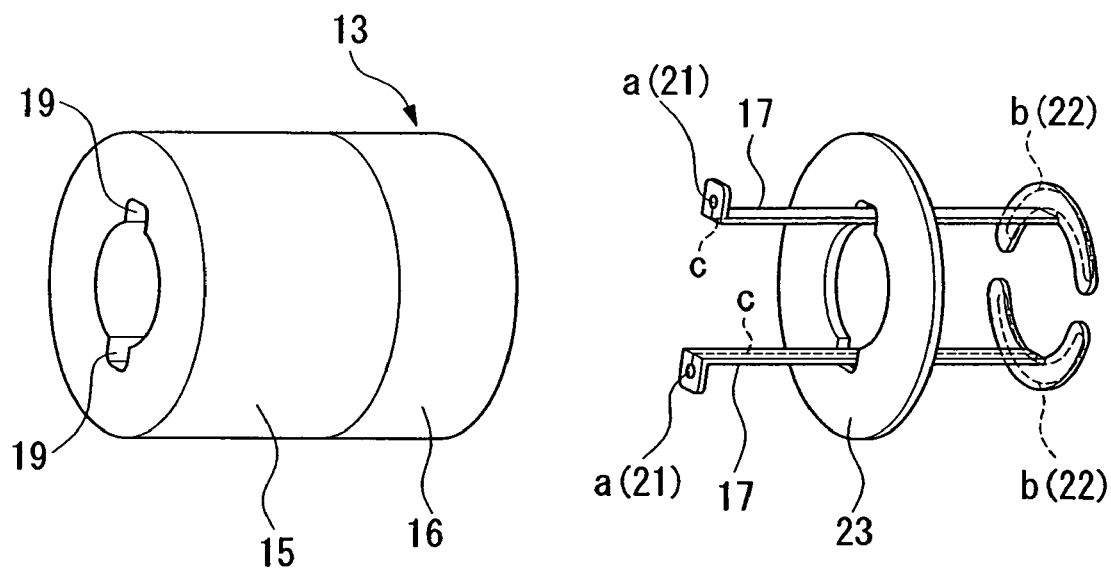
FIG. 3 is an exploded perspective view of the core of first embodiment.
Figure 4:
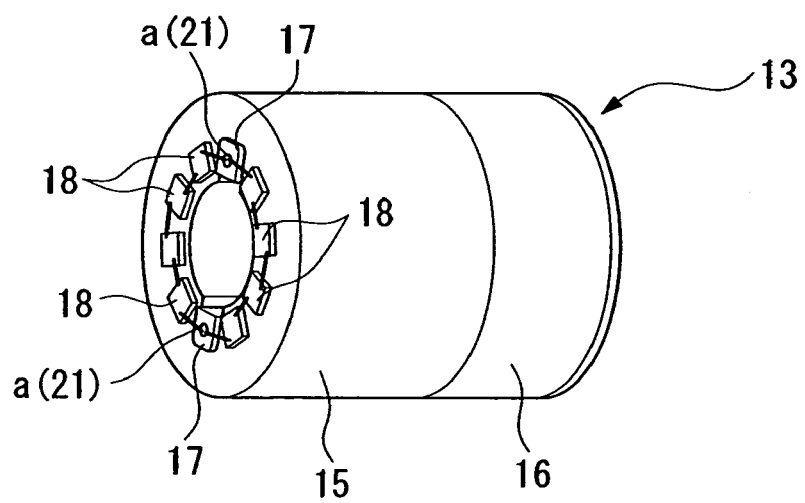
FIG. 4 is a perspective view of the core of first embodiment seen from the front.
Figure 5:
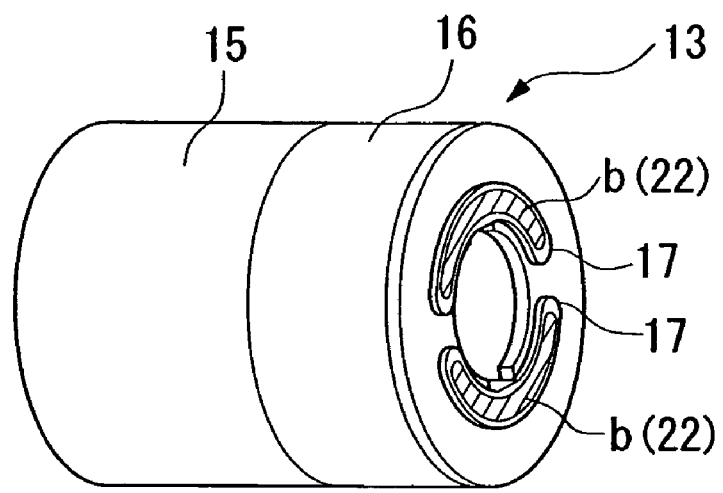
FIG. 5 is a perspective view of the core of first embodiment seen from the back.

The insulating plates 17 each include a substrate made of a flexible insulating material, a pair of metal electrodes a and b, and a connection line c that connects the metal electrodes a and b (see FIG. 3). The pair of metal electrodes a and b and the connection line c are embedded in the substrate. The metal electrodes a and b are exposed from either side of the substrate and form electrode surfaces, respectively. As shown in FIG. 3, the insulating plates 17 have an overall strip shape with a slightly widened tongue shape at one end and a nearly circular arc shape at the other end. The electrode metal a is embedded at one end and electrode metal b at the other end.

The center parts of the insulating plates 17 are fitted in wire guide grooves 19 and 20 formed in the mounting base 15 and rubber elastic body 16. One end of each insulating plate 17 is bent at the front surface of the mounting base 15 and the electrode metal a exposed in the front forms a front electrode terminal 21. The other end of each insulating plate 17 is bent at the rear surface of the rubber elastic body 16 (behind the mounting base 15) and the electrode metal b exposed in the back forms a rear electrode terminal 22. The electrode metal b has an arc shape of a sufficient length in the circumferential direction of the lens adaptor 2. The other end of each insulating plate 17 is attached to one side of a bored disc supporting plate 23. The other side of the supporting plate 23 abuts the rubber elastic body 6. The insulating plates 17 are appropriately fixed to the mounting base 15 by, for example, bonding.

The LED bare chips 18 are circumferentially arranged on the front surface of the mounting base 15 and connected to the front electrode terminals 21 placed on the front surface of the mounting base 15 by wire bonding. In this embodiment, the LED bare chips 18 are blue or purple LEDs and, for example, a YAG (yttrium/aluminum/garnet) fluorescent coating is provided on the front surface of the LED bare chips 18 to obtain white light after the wire bonding.

On the front surface of the mounting base 15 where the LED bare chips 18 and the front electrode terminals 21 are connected as described above, a transmitting glass or resin, bored disc sealing plate 24 is attached as shown in FIG. 1.

The LED illumination unit 13 having the above structure is clamped by an inward flange 25 at the leading edge of the adaptor housing 14 at the front and by a stopper ring 26 at the back and fixed in the adaptor housing 14 as shown in FIG. 1. The stopper ring 26 is fixed at the rear end of the housing 14 after the LED illumination unit 13 is inserted in the adaptor housing 14. The stopper ring 26 has a connection wall 27 extending from the rear end with a stepped part 27a. A cylindrical connection ring 28 is slidably and rotatably fitted on the connection wall 27. The connection ring 28 has an inward stopper flange 29 integrally formed at one end, which abuts the stepped part 27a of the connection wall 27. A first female thread 30 and a second female thread 31 are formed on the inner periphery of the connection ring 28 at predetermined axial intervals.

A fixing male thread 32 is formed on the outer periphery of the coupling plug 9. The first and second female threads 30 and 31 of the connection ring 28 are sequentially screwed on to the male thread 32, by which the lens adaptor 2 can be coupled to the coupling plug 9. An annular conductive rubber 33 is provided on the front side of the power terminals 10A and 10B of the coupling plug 9. Then, the connection ring 28 of the lens adaptor 2 is fitted on the front end of the coupling plug 9 and is rotated in a certain direction, by which the stopper flange 29 abuts the stepped part 27a of the connection wall 27 and restricts the axial movement of the connection ring 28. In this state, the connection ring 28 is further rotated, by which the male thread 32 of the coupling plug 9 is screwed into the first female thread 30 and, then, into the second female thread 31. Consequently, the lens adaptor 2 is coupled to the front end of the coupling plug 9. Here, the power terminals 10A and 10B protruding from the front surface of the coupling plug 9 abut and press the conductive rubber 33, therefore being electrically connected to the rear electrode terminals 22 of the lens adaptor 2 via the conductive rubber 33. When the male thread 32 of the coupling plug 9 is screwed into the second female thread 31, it is disengaged from the first female thread 30. However, the first female thread 30 serves as a stopper to prevent the lens adaptor 2 from falling off in case the screw connection between the male thread 32 and second female thread 31 is loosened.

Figure 6:
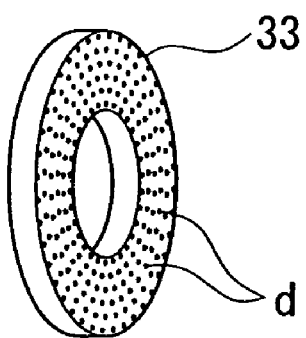
FIG. 6 is a perspective view of the conductive rubber of first embodiment.

The conductive rubber 33 is made of an insulating rubber material such as silicon rubber where a conductive material d such as nickel particles and gold-plated metal particles is embedded in dots as shown in FIG. 6, and generally is referred to as a dot-type anisotropic conductive rubber. When the rubber material of the conductive rubber 33 having the above structure is pressed across the thickness, the conductive rubber 33 has increased conductivity where the density of the conductive material d is increased as a result of compressive deformation and, therefore, becomes conductive through the thickness. However, because the rubber material is insulating, the conductive rubber 33 is still insulated in any direction (for example the circumferential direction) except for through the thickness.

As shown in FIG. 1, a positioning projection 34 is provided on the inner periphery of the connection wall 27 of the lens adaptor 2 and a receiving groove 35 is provided on the outer periphery of the coupling plug 9. When the lens adaptor 2 and the coupling plug 9 are coupled, the positioning projection 34 and receiving groove 35 are engaged, by which their peripheral positions are precisely aligned.

In the endoscope of this embodiment having the structure above, the insulating plates 17 having a pair of metal electrodes a and b and a connection line c that connects the metal electrodes a and b embedded therein are used to provide the front and rear electrode terminals 21 and 22 that are placed at the front and at the back of the mounting base 15, respectively, and connected to each other. Therefore, compared to the prior art in which the electrode terminals at the front and back of the mounting base are soldered to either end of a wire, the placement and connection of electrodes is significantly facilitated in assembling the insulating plate 17 into mounting base 15 and, therefore, assembly efficiency of the endoscope is remarkably improved. Improving the assembly efficiency is useful for down-sizing the insertion section 3 including the lens adaptor 2.

In the endoscope of this embodiment, the insulating plates 17 are made of a flexible material. The insulating plate 17 is easily bent near the front electrode terminal 21 and near the rear electrode terminal 22. Being flexibly deformed, the insulating plate 17 can be easily housed in a limited space within the LED illumination unit 13, which also contributes to the improved assembly efficiency in the endoscope of this embodiment. However, the insulating plate 17 is not necessarily made of a flexible material. The insulating plate 17 can be made of a hard material and easily bent near the front electrode terminal 21 and near the rear electrode terminal 22.

In the endoscope of this embodiment, the rubber elastic body 16 is interposed between the rear electrode terminals 22 and the mounting base 15, by which the rear electrode terminals 22 are supported by the rubber elastic body 16 at the back. When the lens adaptor 2 is coupled to the coupling plug 9 and the conductive rubber 33 is pressed against the rear electrode terminals 22, the rubber elastic body 16 is flexibly deformed together with the insulating plates 17. Consequently, the power terminals 10A and 10B and the rear electrode terminals 22 are reliably connected without causing any damage to or deterioration of components of the lens adaptor 2 and coupling plug 9. When the rubber elastic body 16 is interposed between the rear electrode terminals 22 and the mounting base 15 as in this embodiment, the conductive rubber 33 can be eliminated.

Figure 7:
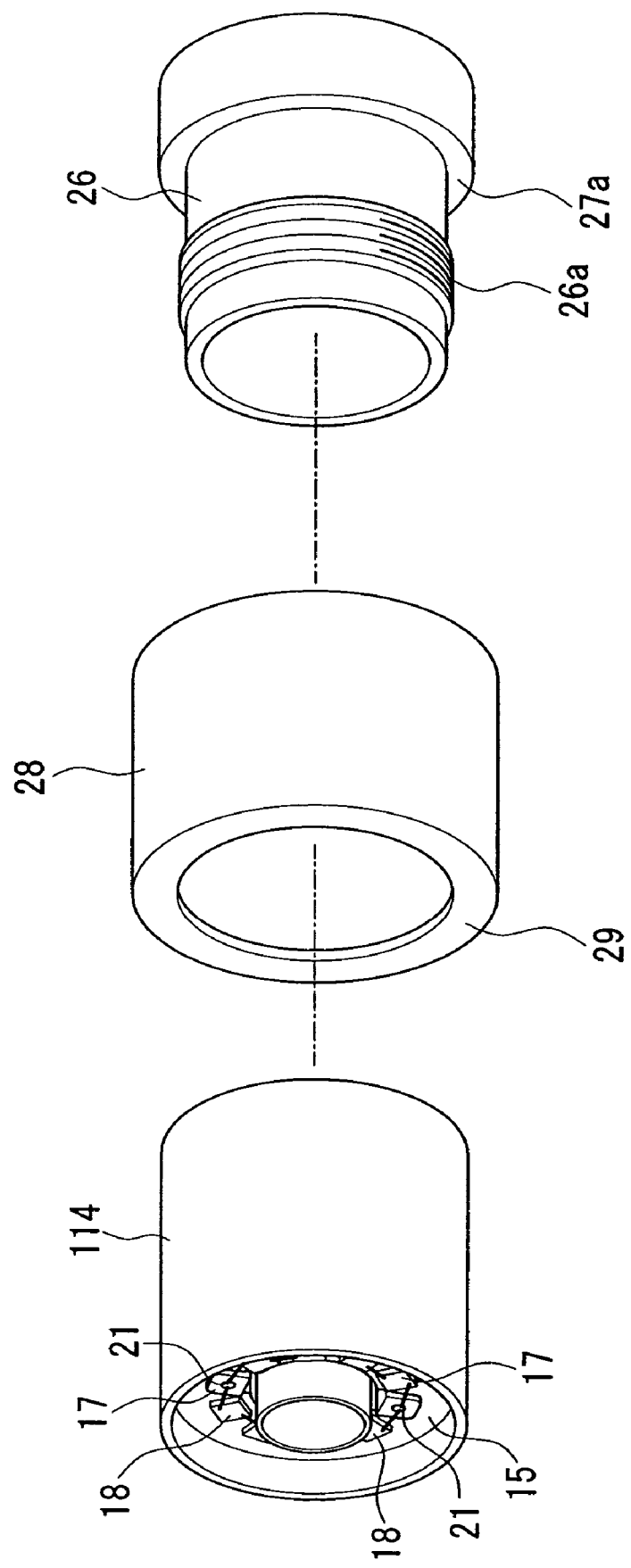
FIG. 7 is an exploded perspective view of the core showing second embodiment of the present invention.

FIG. 7 shows second embodiment of the endoscope of the present invention.

The mounting base 15 is separately formed from the adaptor housing 14 in the endoscope of first embodiment. On the other had, as shown in FIG. 7, the mounting base 15 is integrally formed with an adaptor housing 114 in the endoscope of this embodiment. A female thread (not shown) is formed in the adaptor housing 114. The female thread is screwed onto a male thread 26a of the stopper ring 26. The connection ring 28 is rotatably supported between the adaptor housing 114 and the stopper ring 26.

FIG. 8 shows third embodiment of the endoscope of the present invention.

Figure 8A:
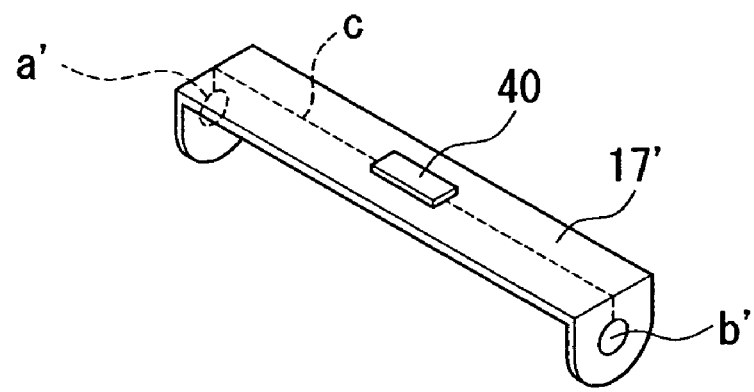
FIG. 8A is a perspective view of an insulating plate showing third embodiment of the present invention.

In the endoscope of this embodiment, as shown in FIG. 8A, a temperature sensor 40 for detecting the temperature around the LEDs is fixed to an insulating plate 17' where the metal electrodes a and b and connection line c are embedded. Wires for the temperature sensor 40 can be easily added to the insulating plate 17' when the metal electrodes a' and b' and connection line c are embedded therein. Therefore, the insulating plate 17' can be produced at reduced cost. Furthermore, the temperature sensor 40 can be easily placed near the LED. The temperature sensor 40 constantly detects the temperature around the LED to prevent noise in CCD image signals caused by an overheated LED.

In the endoscope of this embodiment, the temperature sensor 40 is fixed to the insulating plate 17'. Besides the temperature sensor 40, a pressure sensor or a humidity sensor, or an acceleration sensor for detecting the gravity direction can also be fixed. The pressure or humidity sensor is placed in the lens adaptor 2 so as to detect changes in pressure or humidity within the lens adaptor 2 when moisture or external air enters the lens adaptor 2 because of defects of the lens adaptor 2. Alternatively, the pressure or humidity sensor is placed at a communicating point to the outside of the lens adaptor 2 so as to detect changes in pressure or humidity around the lens adaptor 2 that occur in the course of examination. The acceleration sensor detects the gravity acceleration so as to detect the orientation and inclination about the axis of the lens adaptor 2.

Figure 8B:
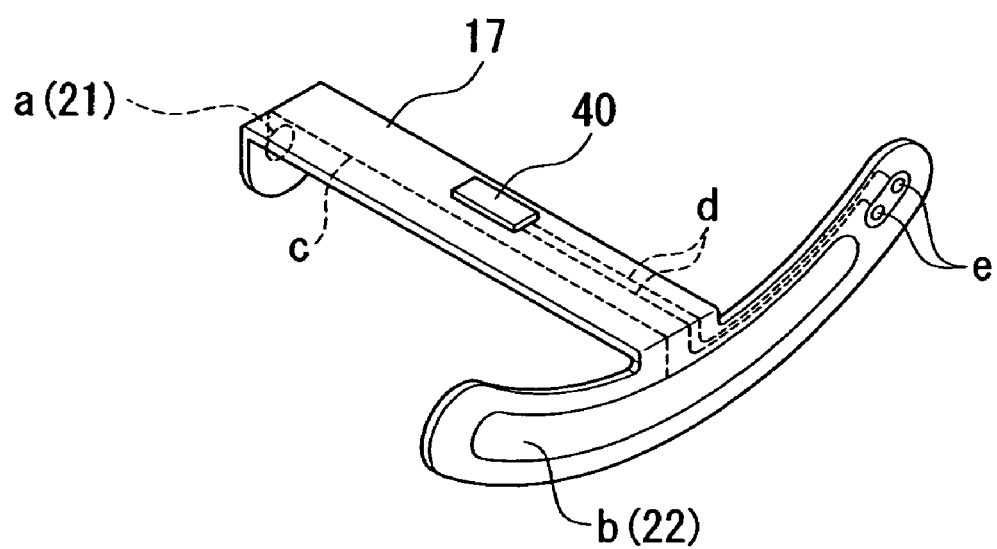
FIG. 8B is a perspective view of an insulating plate when third embodiment is applied to first embodiment.

The structure of this embodiment can be applied to first embodiment. Specifically, as shown in FIG. 8B, the temperature sensor 40 can be fixed to the insulating plate 17 used in first embodiment. Further, terminals e for the temperature sensor 40 are provided at the arc part of the insulating plate 17 and connection lines d between the temperature sensor 40 and the terminals e can be embedded in the insulating plate 17.

Figure 9:
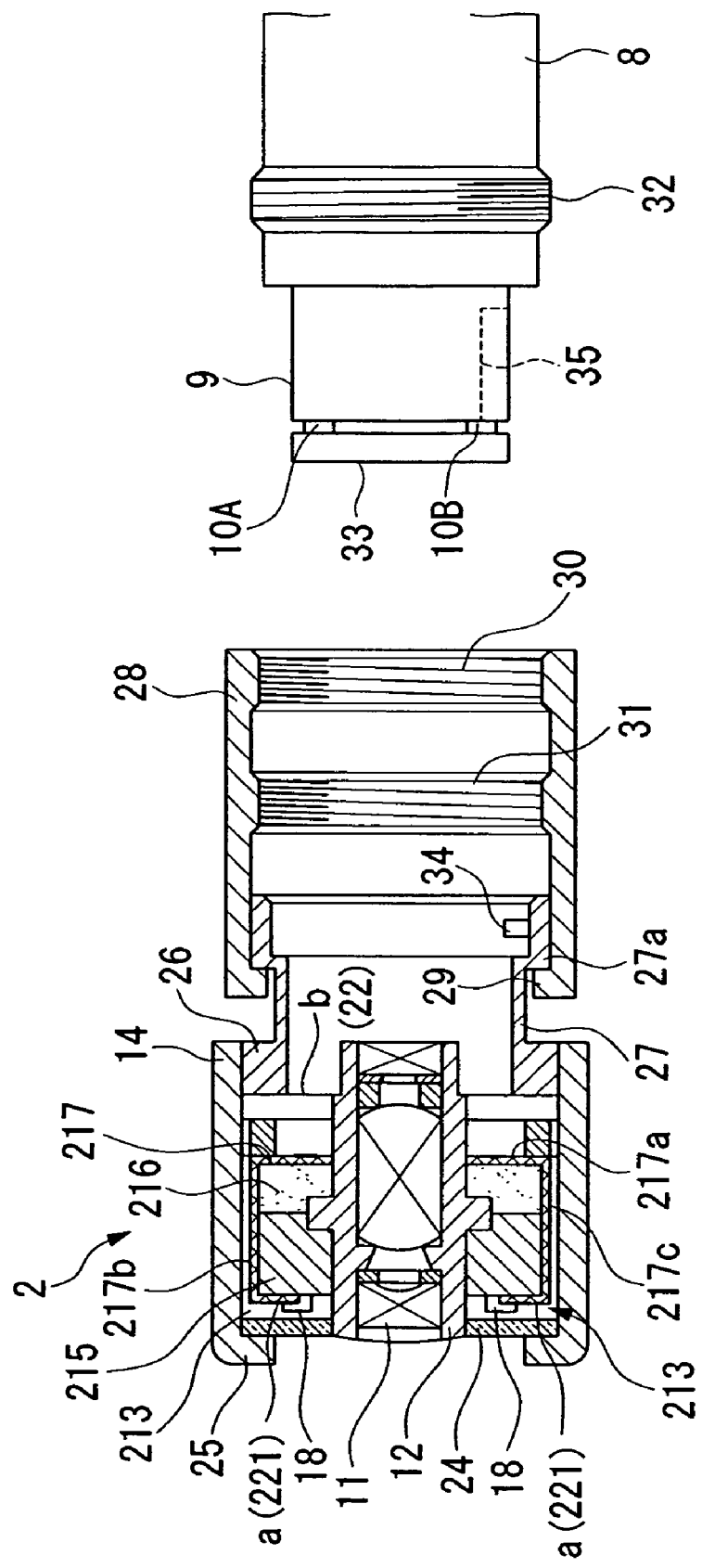
FIG. 9 is a vertical cross-sectional view of the core showing fourth embodiment of the present invention.
Figure 10:
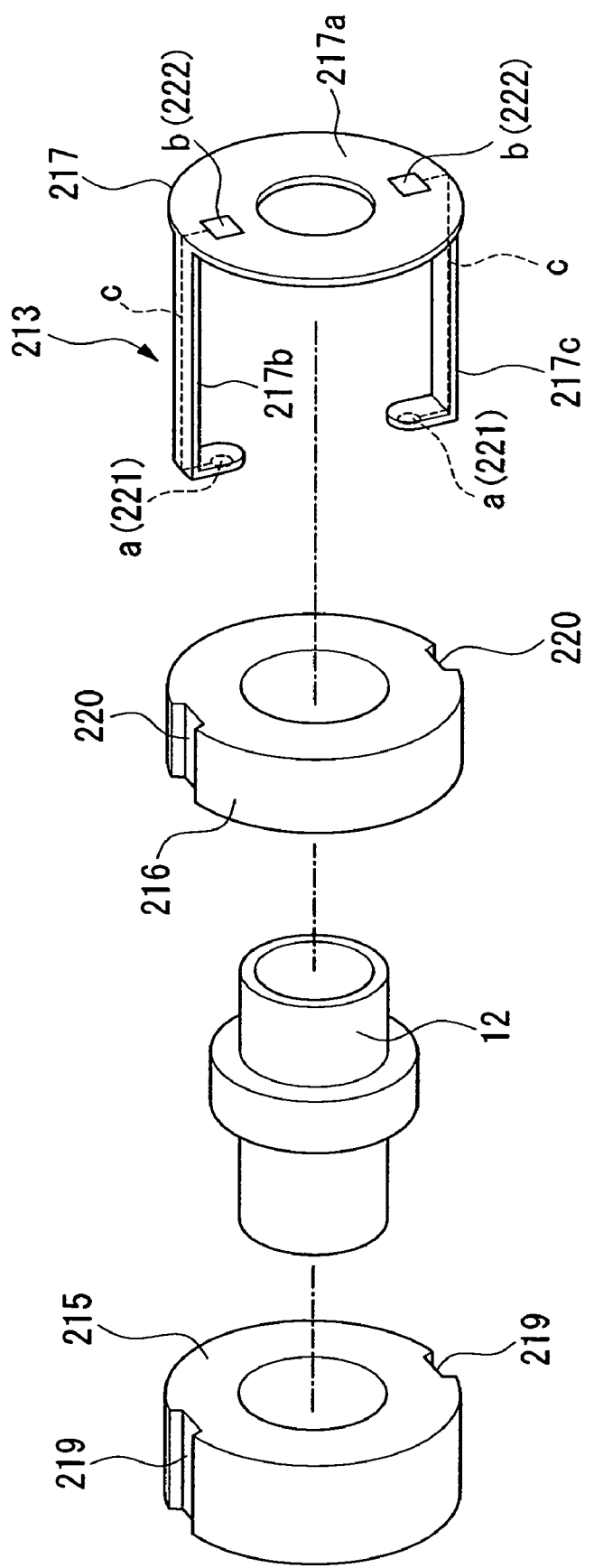
FIG. 10 is an exploded perspective view of the core showing fourth embodiment.
Figure 11:
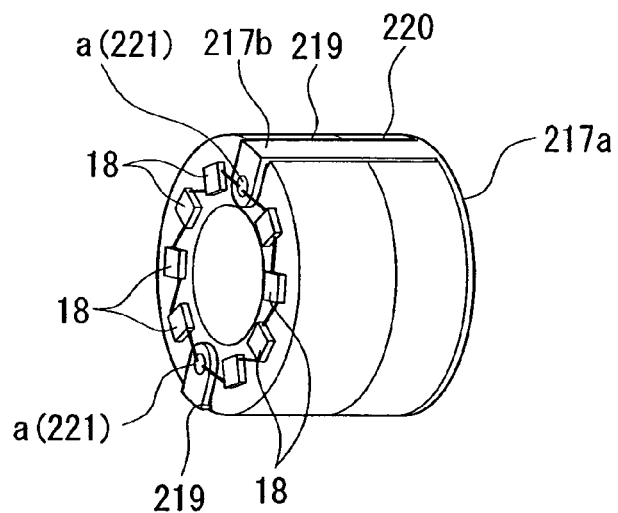
FIG. 11 is a perspective view of the core showing fourth embodiment.

FIGS. 9 to 11 show fourth embodiment of the endoscope of the present invention.

The endoscope of this embodiment has nearly the same basic structure as the endoscope of first embodiment. However, an LED illumination unit 213 housed in the adaptor housing 14 includes components having slightly different shapes.

A mounting base 215 and a rubber elastic body 216 have a bored disc shape as in the endoscope of first embodiment. However, wire guide grooves 219 and 220 are formed on the outer periphery of the mounting base 215 and rubber elastic body 216, not on their inner periphery. One insulating plate 217 is provided in the endoscope of this embodiment while two identical insulating plates 17 are provided in the endoscope of first embodiment.

The insulating plate 217 consists of a bored disc substrate 217a and a pair of strip-shaped extended parts 217b and 217c. The substrate 217a is fixed on the back of the rubber elastic body 216. The extended parts 217b and 217c are extended from the outer perimeter of the substrate 217a in the axial direction of the lens adaptor 2. The tips of the extended parts 217b and 217c are bent inward in the radial direction of the substrate 217a. The electrode metal a is embedded in the front surface of the tip of each extended part 217b. Two metal electrodes b are embedded in the rear surface of the substrate 217a, each corresponding to the electrode metal a provided at the extended part 217b. The metal electrodes a and b are partly exposed from the surface of the insulating plate 217. The metal electrodes a and b are connected by a connection line c embedded in the extended part 217b. The electrode metal a forms a front electrode terminal 221 and the electrode metal b forms a rear metal terminal 222.

The endoscope of this embodiment yields the same efficacy as first embodiment. In addition, two pairs of electrode terminals (front electrode terminals 221 and rear electrode terminals 222) are provided integrally with one insulating plate 217; therefore, the number of components is reduced compared to the endoscope of first embodiment. Therefore, assembly of the endoscope is facilitated. In the endoscope of this embodiment, the wire guide grooves 219 and 220 are formed on the outer periphery of the mounting base 215 and rubber elastic body 216 and the extended part 217b and 217c of the insulating plate 217 are placed in the wire guide grooves 219 and 220; therefore, it is easier to process the wire guide grooves 219 and 220 and place the insulating plate 217 compared to the endoscope of first embodiment.

Figure 12:
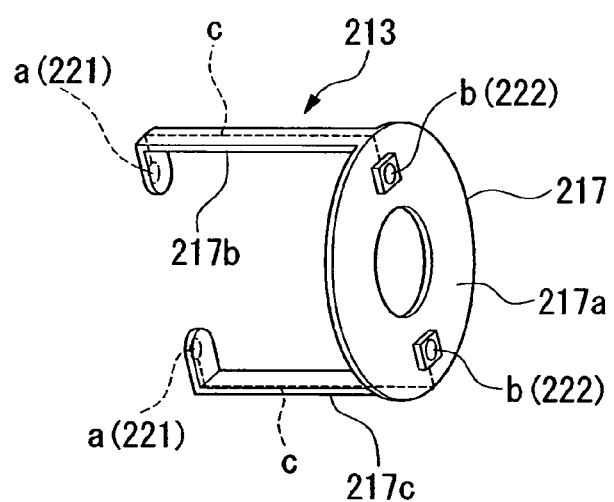
FIG. 12 is a perspective view of an insulating plate showing fifth embodiment of the present invention.

FIG. 12 shows fifth embodiment of the endoscope of the present invention.

The substrate 217a of the insulating plate 217 is flat in the endoscope of fourth embodiment. On the other hand, as shown in FIG. 12, rear electrode terminals 222 of the insulating plate 217 protrude in the endoscope of this embodiment and the rear electrode terminals 222 are elastically deformed in the axial direction of the lens adaptor 2.

Figure 13:
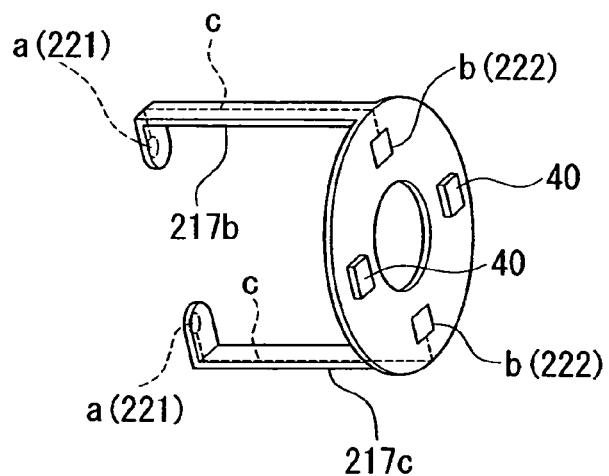
FIG. 13 is a perspective view of an insulating plate showing sixth embodiment of the present invention.

FIG. 13 shows sixth embodiment of the endoscope of the present invention.

In the endoscope of this embodiment, as shown in FIG. 13, the temperature sensor 40 is provided on the rear surface of the insulating plate 217 integrally therewith as in the endoscope of third embodiment.

Figure 14:
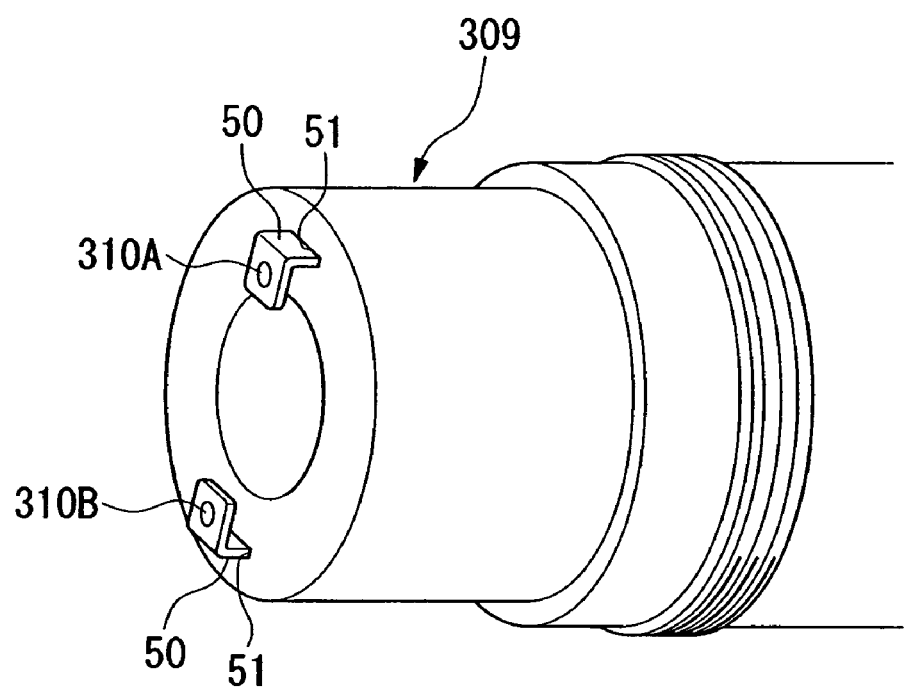
FIG. 14 is a perspective showing seventh embodiment of the present invention.
Figure 15:
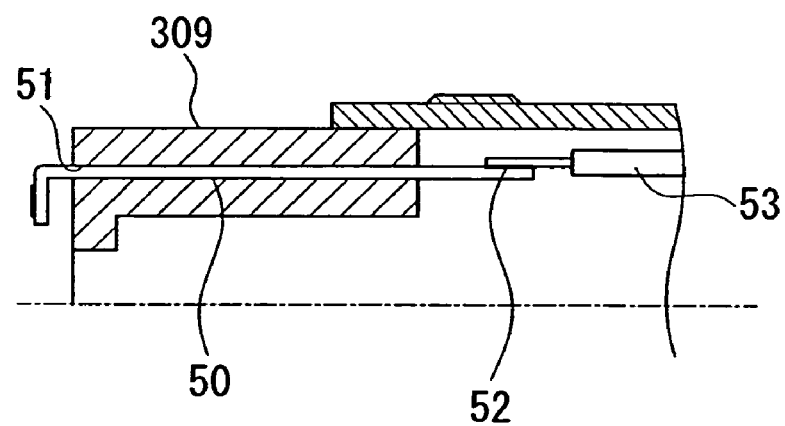
FIG. 15 is a vertical cross-sectional view showing seventh embodiment.
Figure 16:
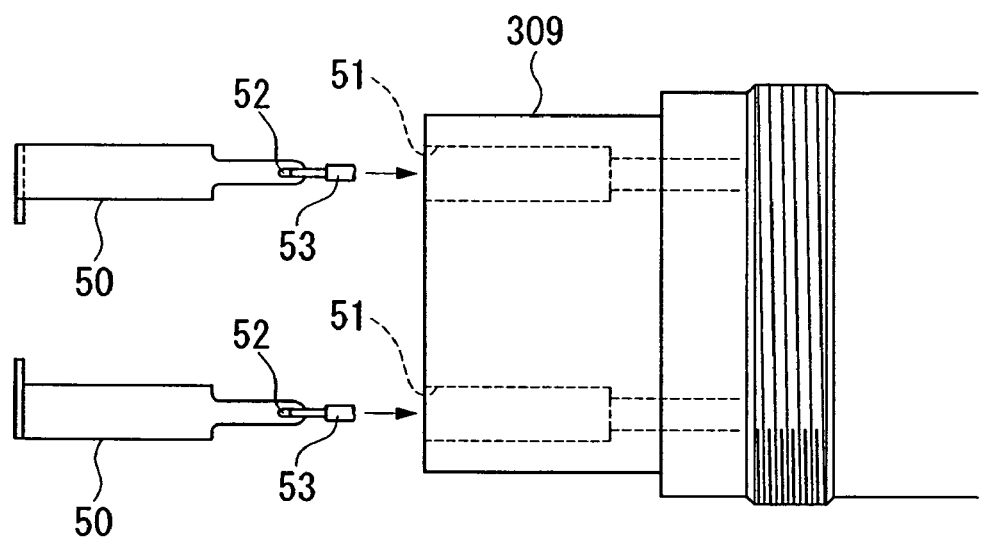
FIG. 16 is a plane view showing seventh embodiment.

FIGS. 14 to 16 show seventh embodiment of the endoscope of the present invention.

In the endoscope of this embodiment, a coupling plug 309 has modified power electrodes 310A and 310B. The lens adaptor has the same structure as any of the above embodiments. The power electrodes 310A and 310B of the coupling plug 309 are embedded in the tips of insulating plates 50 made of a flexible material. The insulating plates 50 are inserted in mounting holes 51 formed in the distal end of the coupling plug 309. The insulating plates 50 have a strip shape. The power electrodes 310A and 310B are embedded in the insulating plates 50 at one end and connection terminals 52 at the other end. The power electrode 310A or 310B embedded in the insulating plate 50 and the connection terminal 52 are connected by a connection line (not shown) embedded in the insulating plate 50.

One end of the insulating plate 50 protrudes forward from the coupling plug 309 through the mounting bore 51. The part of the insulating plates 50 where the power electrode 310A or 310B is placed is bent inward in the radial direction of the coupling plug 309. The connection terminal 52 on the other end of the insulating plate 50 is connected to a lead line 53 provided in the flexible tube.

In the endoscope of this embodiment, the power electrodes 310A and 310B are embedded in one end of the insulating plates 50; therefore, the power electrodes 310A and 310B are easily provided and a cushioning effect by the insulating plates 50 can be obtained when the power electrodes 310A and 310B are connected to the electrodes on the lens adaptor 2.

Figure 17:
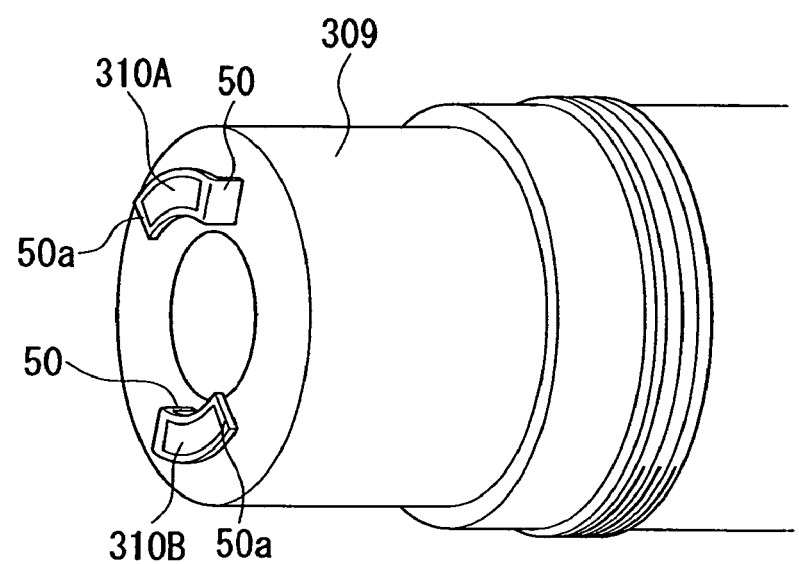
FIG. 17 is a perspective view showing a modified embodiment of seventh embodiment.

In the endoscope of this embodiment, one end of the insulating plates 50 is bent inward in the radial direction of the coupling plug 309. As shown in FIG. 17, bent parts 50a bending in the peripheral direction of the coupling plug 309 can be formed at one end of the insulating plates 50, by which the power electrodes 310A and 310B are placed at the bent parts 50a. In this way, the power electrodes 310A and 310B can have an arc shape, being sufficiently extended in the peripheral direction.

Figure 18A:
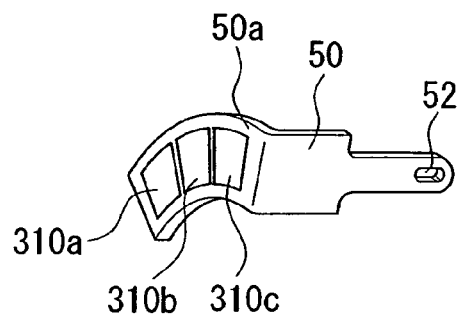
FIG. 18A is a perspective view showing another modified embodiment of seventh embodiment.

Furthermore, being formed at the one end of the insulating plates 50, the bent parts 50a bending in the peripheral direction of the coupling plug 309 can be extended in the peripheral direction enough to provide multiple different power electrodes 310a, 310b, and 310c on the bent parts 50a as shown in FIG. 18A. By placing multiple different power electrodes 310a, 310b, and 310c on the bent part 50a, power sources of different voltages can be selectively used depending on applications. If the rear electrode terminals are placed at different positions according to the adaptor type, the adaptor type can be recognized by, for example, a controller provided in the take-up drum when the adaptor is replaced.

Figure 18B:
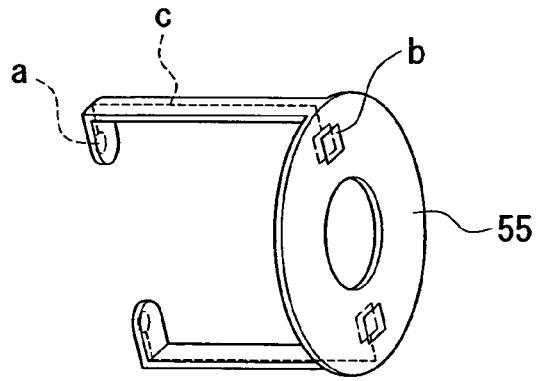
Figure 18C:
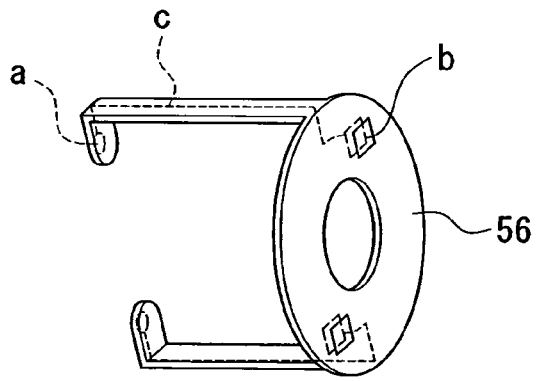
Figure 18D:
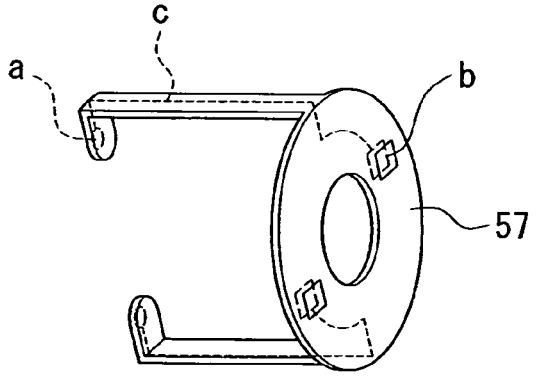

For example, FIGS. 18B to 18D show insulting plates having different shapes. Specifically, an insulating plate 55 shown in FIG. 18B, an insulating plate 56 shown in FIG. 18C, and an insulating plate 57 shown in FIG. 18D are different in the position of the metal electrodes b to be connected to the power electrode of the insertion section. The electrodes b of the insulating plate 56 are shifted from the metal electrodes b of the insulation plate 55 in one peripheral direction. The metal electrodes b of the insulating plate 57 are further shifted from the electrodes b of the insulation plate 56 in one peripheral direction. The metal electrodes b of the insulating plate 55 are connected to the power electrodes 310c of the insulating plate 50 shown in FIG. 18A; the metal electrodes b of the insulating plate 56 are connected to the power electrodes 310b of the insulating plate 50; and the electrodes b of the insulating plate 57 are connected to the power electrode 310a of the insulating plate 50. In this way, the metal electrodes b on the adaptor can be placed at different positions according to the adaptor type, by which the type of the adaptor mounted at the tip of the insertion section can be recognized by a controller on hand. Different types of adaptors can be controlled as required.

Figure 19:
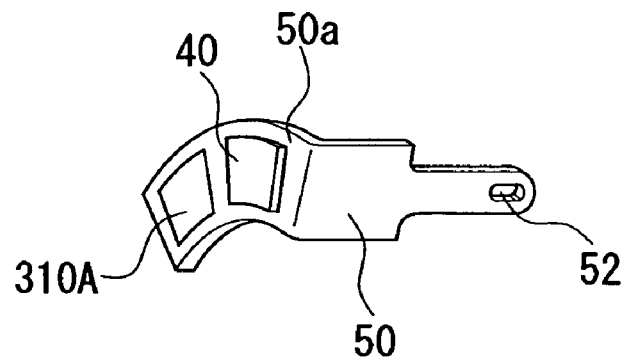
FIG. 19 is a perspective view showing further another modified embodiment of seventh embodiment.

Further, when the bent parts 50a bending in the peripheral direction of the coupling plug 309 are formed at one end of the insulating plates 50, as shown in FIG. 19, the temperature sensor 40 can be provided on the bent part 50a along with the power electrode 310A.

Figure 20:
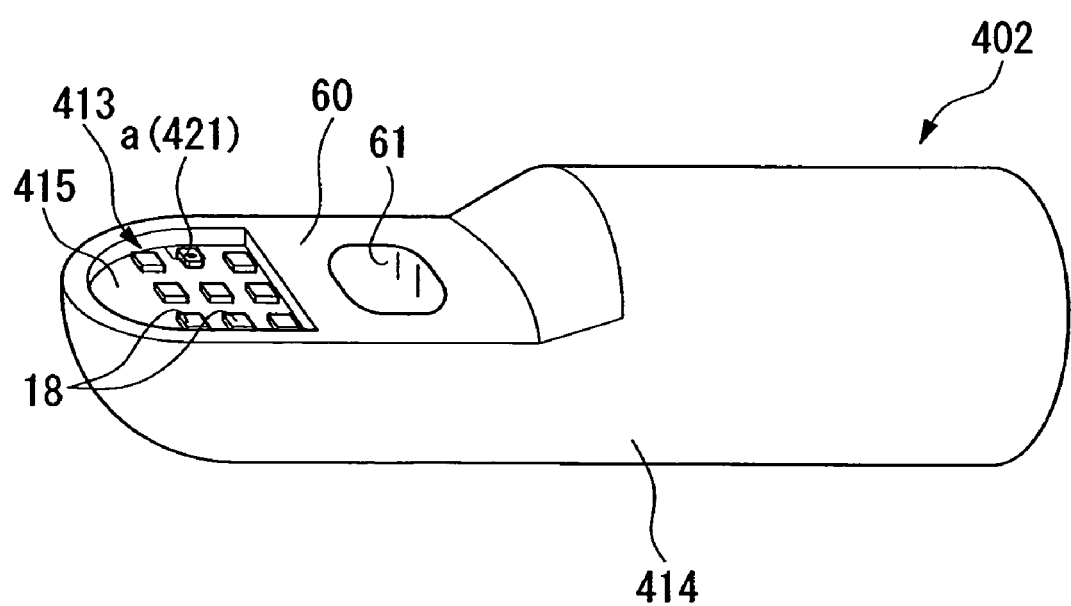
FIG. 20 is a perspective view showing eighth embodiment of the present invention.
Figure 21:
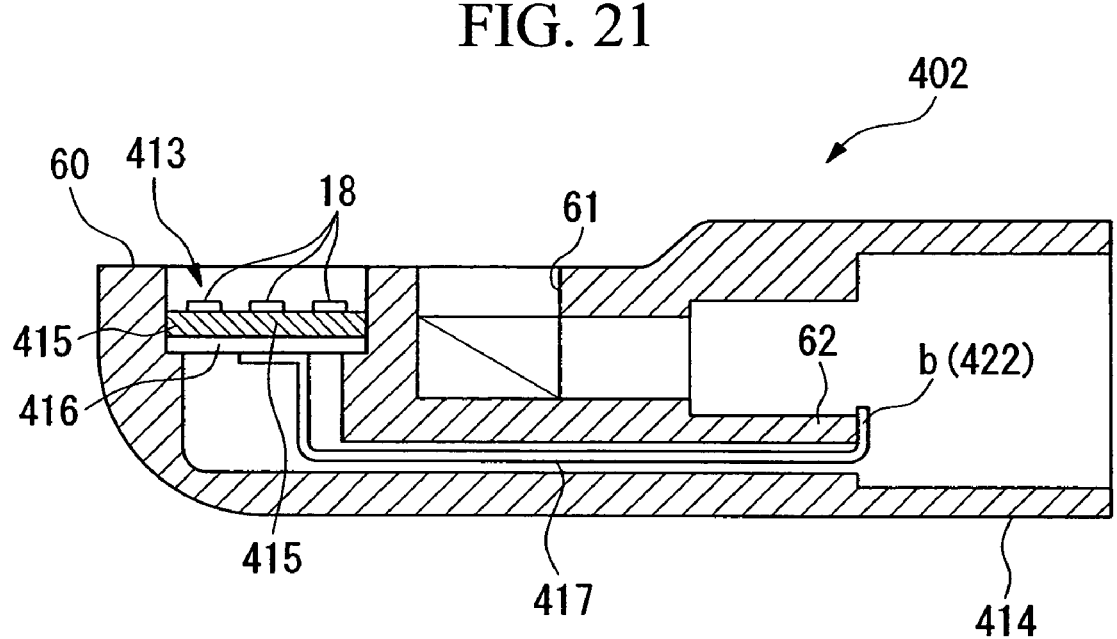
FIG. 21 is a vertical cross-sectional view showing eighth embodiment.
Figure 22:
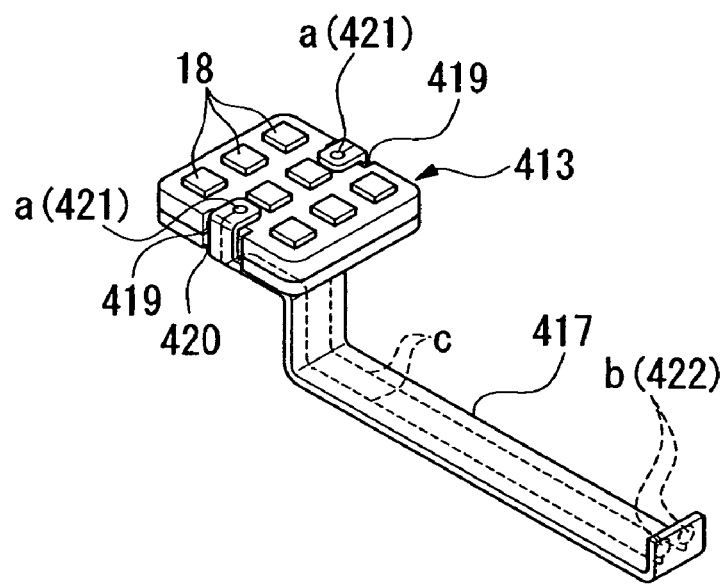
FIG. 22 is a perspective view of the core showing eighth embodiment.

FIGS. 20 to 22 show eighth embodiment of the endoscope of the present invention.

In the endoscope of this embodiment, the basic structure of the endoscope of the present invention is applied to a side-view type lens adaptor 402. As shown in FIGS. 20 and 21, an adaptor housing 414 has a stepped side surface 60 at the distal end. An imaging window 61 and an LED illumination unit 413 are provided on the stepped surface 60 in parallel.

The LED illumination unit 413 includes a mounting base 415, a rubber elastic body 416, and a pair of insulating plates 417 similarly to the other aforementioned embodiments. The mounting base 415 has multiple LED bare chips attached to the front surface. The rubber elastic body 416 is fixed on the back of the mounting base 415. Electrode metals a and b and a connection line c connecting the metal electrodes a and b are embedded in the insulating plate 417. The mounting base 415 and rubber elastic body 416 have a nearly square shape. As shown in FIG. 22, the insulating plate 417 has a strip shape. The insulating plate 417 is placed along wire guide grooves 419 and 420 formed on either side of the mounting base 415 and rubber elastic body 416, bent at the rear end of the rubber elastic body 416, and latched to a supporting wall 62 at the base end of the adaptor housing 414. Also in the endoscope of this embodiment, the electrode metal a provided at one end of the insulating plate 417 forms a front electrode terminal 421 connected to the LED bare chips 18 and the electrode metal b provided at the other end of the insulating plate 417 forms a rear electrode terminal 422 connected to the power part on the coupling adaptor.

The endoscope of this embodiment is different in shape from the endoscope of fourth embodiment shown in FIGS. 9 to 11. However, it yields nearly the same efficacy.

Figure 23:
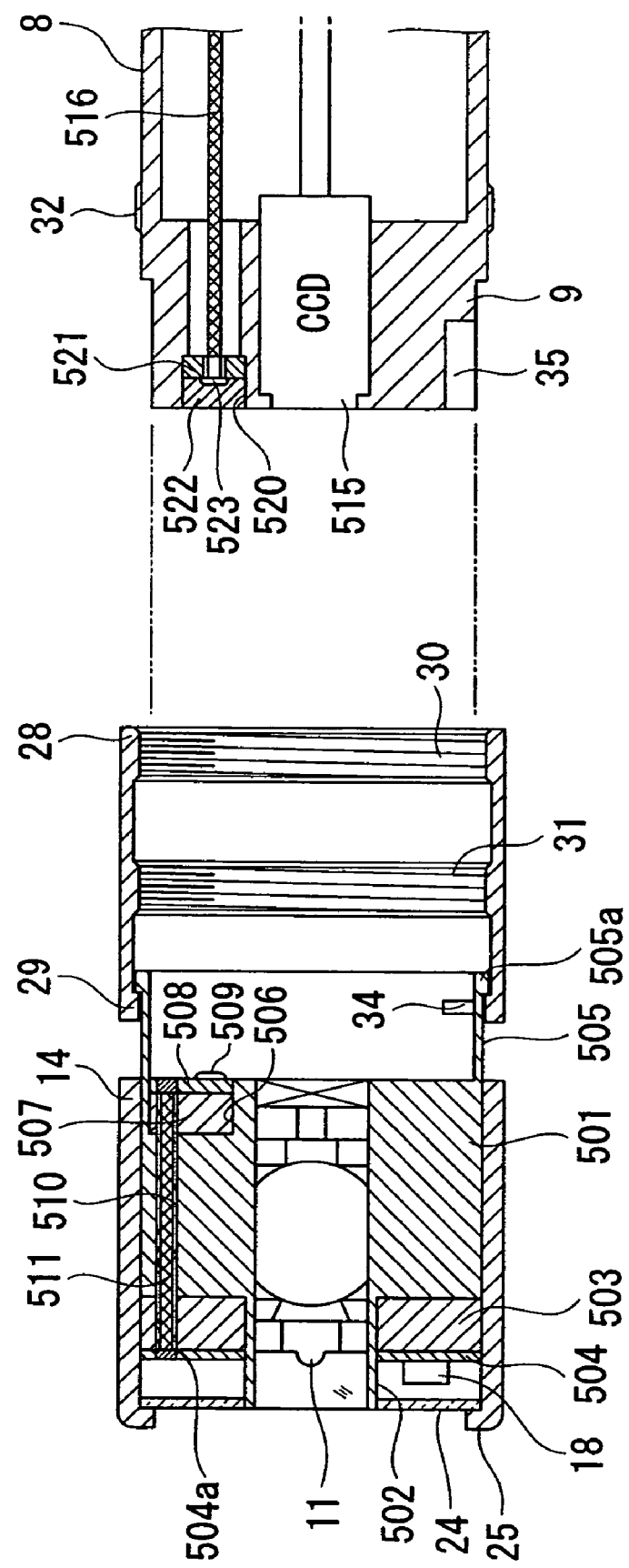
FIG. 23 is a vertical cross-sectional view of the core showing ninth embodiment of the present invention.
Figure 24:
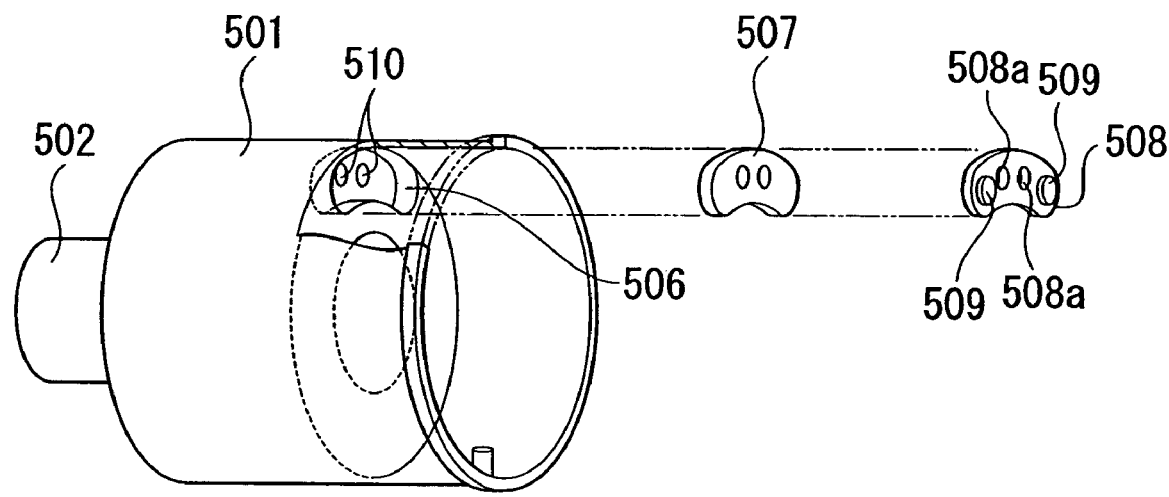
FIG. 24 is a perspective view of the lens barrel provided in the endoscope of ninth embodiment.
Figure 25:
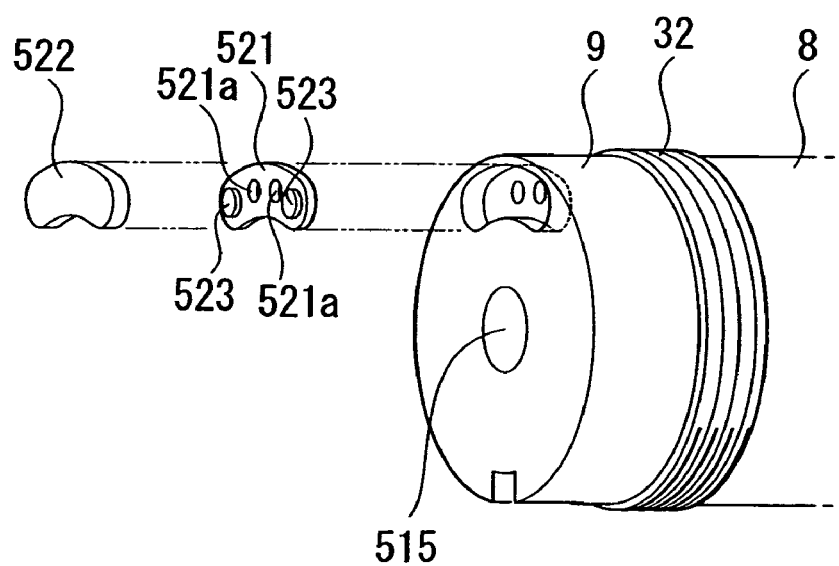
FIG. 25 is a perspective view of the insertion section distal end of the endoscope of ninth embodiment.

FIGS. 23 to 25 show ninth embodiment of the endoscope of the present invention.

In the endoscope of this embodiment, as shown in FIG. 23, a solid lens barrel 501 for housing an objective lens group 11 is provided inside the adaptor housing 14. The lens barrel 501 is solid and has an outer diameter nearly equal to the inner diameter of the adaptor housing 14. The lens barrel 501 is inserted in the adaptor housing 14 and fixed therein by, for example, bonding. The lens barrel 501 has on the front surface a smaller diameter part 502 protruding in the axial direction of the lens adaptor 2 and integrally formed. An aluminum substrate 503 having a bored disc shape and an insulating plate (a first flexible insulating plate) 504 having nearly the same shape as the substrate 503 are fitted on the smaller diameter part 502 with the insulating plate 504 in front of the substrate 503.

The insulating plate 504 is made of a flexible insulating material and has LED bare chips 18 bonded to the front surface. The outer diameter of the substrate 503 and insulating plate 504 is nearly equal to the inner diameter of the adaptor housing 14. The inner diameter of the bores of the substrate 503 and insulating plate 504 is nearly equal to the outer diameter of the smaller diameter part 502. The substrate 503 and insulating plate 504 are inserted in an annular space between the adaptor housing 14 and the smaller diameter part 502.

The lens barrel 501 has a connection wall 505 integrally formed on the back. The connection wall 505 has a thin-wall cylinder shape having an outer diameter nearly equal to the outer diameter of the lens barrel 501. The connection wall 505 is provided with a stepped part 505a at the rear end. The stopper flange 29 of the connection ring 28 is engaged with the stepped part 505a. As shown in FIG. 24, the lens barrel 501 has an arc hole 506 on the rear surface. A small aluminum substrate 507 having nearly the same shape as the hole 506 and an insulating plate 508 having nearly the same shape as the hole 506 are inserted in the hole 506. The insulating plate 508 is placed behind the small substrate 507. Adaptor's side electrodes (adaptor's side electrode terminals) 509 are fixed to the rear surface of the insulating plate.

Two through-holes 510 running in the axial direction of the lens adaptor 2 are formed in the lens barrel 501, substrate 503, insulating plate 504, small substrate 507, and insulating plate 508 placed inside the adaptor housing 14.

Two through-holes 504a, which are a part of the through-hole 510, are formed in the insulating plate 504. Electrodes (not shown) are provided on the inner periphery of the through-holes 504a, respectively. Each electrode is connected to the LED bare chips 18 bonded to the front surface of the insulating plate 504 via a connection line (not shown) embedded in the insulating plate 504.

Two through-holes 508a, which include a part of the through-hole 510, are formed in the insulating plate 508. Electrodes (not shown) are provided on the inner periphery of the through-holes 508a, respectively. Each electrode is connected to the adaptor's side electrode 509 fixed to the rear surface of the insulating plate 508 via a connection line (not shown) embedded in the insulating plate 508.

An electric line 511 is inserted in each of the two through-holes 510. One end of the electric line 511 is soldered to the electrode provided on the inner periphery of the through-hole 504a of the insulating plate 504. The other end of the electric line 511 is soldered to the electrode provided on the inner periphery of the through-hole 508a of the insulating plate 508. Consequently, the LED bare chips 18 and the adaptor's side electrodes 509 are electrically connected.

As shown in FIG. 25, a CCD 515 is provided on the leading surface of the coupling plug 9 at the center. An arc hole 520 is further formed on the leading surface of the coupling plug 9 around the CCD 515. The hole 520 has nearly the same shape as the hole 506 of the lens adaptor 2. An insulating plate (a second flexible insulating plate) 521 having nearly the same shape as the hole 520 and a conductive rubber 522 (power supply pad) having nearly the same shape as the hole 520 are inserted in the hole 520 with the conductive rubber 522 in front of the insulating plate 521. Insertion part's side electrodes 523 are fixed to the front surface of the insulating plate 521.

Two through-holes 521a running in the axial direction of the coupling plug 9 are formed in the insulating plate 521. Electrodes (not shown) are provided on the inner periphery of the through-holes 521a. Each electrode is connected to the insertion section's side electrodes 523 fixed to the front surface of the insulating plate 521 via a connection line (not shown) embedded in the insulating plate 521. The distal ends of two electric lines 516 (power supply lines) provided in the insertion section are inserted into the through-holes 521a, respectively. The ends of the electric lines 511 are soldered to the electrodes provided on the inner periphery of the through-holes 504a. Therefore, the insertion section's side electrodes 523 can be powered via the electric lines placed in the insertion section.

The conductive rubber 522 has the same inner structure as the conductive rubber 33 of first embodiment. The conductive rubber 522 becomes conductive through the thickness when it receives a compressive force in the thickness direction.

The endoscope having the above structure is assembled as follows. First, the objective lens group 11 is installed in the lens barrel 501. The smaller diameter part 502 of the lens barrel 501 is inserted in the bores of the substrate 503 and insulating plate 504. The substrate 503 and insulating plate 504 are latched to the front surface of the lens barrel 501. The small substrate 507 and insulating plate 508 are fitted in the bore 506. The electric lines 511 are inserted into the two through-holes 510 and soldered to the electrodes in the through-holes 504a of the insulating plate material 504 at one end and to the electrodes in the through-holes 508a of the insulating plate 508 at the other end.

Then, the transmitting sealing plate 24 is placed in the adaptor housing 14 and, then, the lens barrel 501 is inserted therein. The outer periphery of the lens barrel 501 is bonded to the inner periphery of the adaptor housing 14.

In the endoscope having the above structure, when the lens adaptor 2 is attached to the distal end of the insertion section, the adaptor's side electrode 509 is pressed against the conductive rubber 522 and the conductive rubber 522 receives a compressive force in the thickness direction. Therefore, the adaptor's side electrode 509 and the insertion section's side electrode 523 are electrically connected via the conductive rubber 522.

The endoscope of this embodiment significantly facilitates the placement and connection of electrodes compared to the prior art, remarkably improving assembly efficiency of the endoscope. Improving the assembly efficiency is very useful for down-sizing the insertion section 3 including the lens adaptor 2.

In this embodiment, the through-holes 504a are formed in the insulating plate 504, the electrodes are provided on the inner periphery of the through-holes 504a, and, the electrodes are soldered to the ends of the electric lines 511. However, the electrodes can be provided on the rear surface of the insulating plate 504 and soldered to the ends of the electric lines 511 without forming the through-holes 504a. Alternatively, the through-holes 504a are formed, with electrodes provided on the front surface of the insulating plate 504, and the ends of the electric lines are protruded from the through-holes 504a and, then bent. Then, the electrodes provided on the front surface of the insulating plate 504 are soldered to the ends of the electric lines 511. The insulating plate 508 can be similarly modified.

Figure 26:
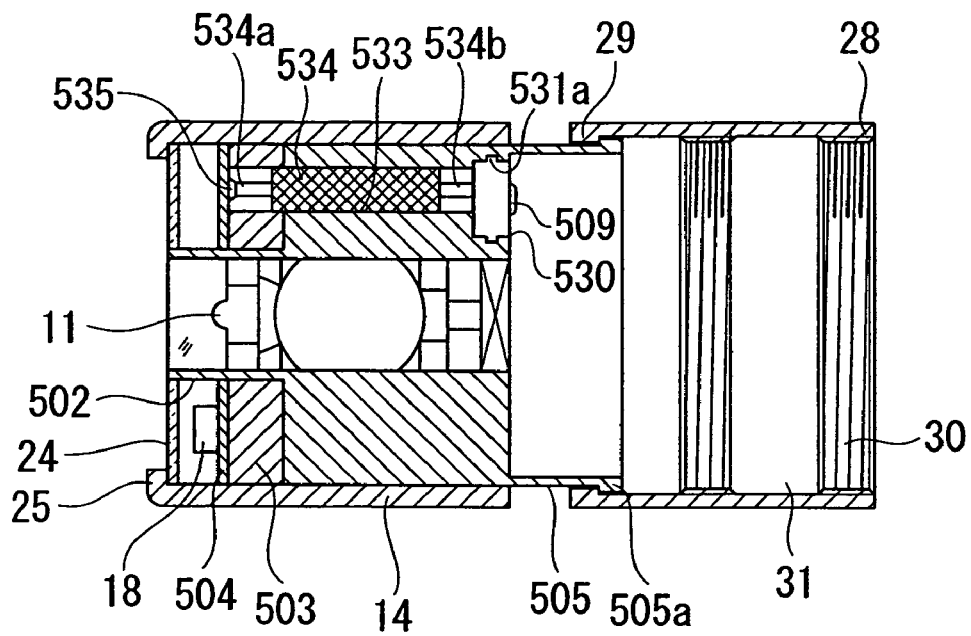
FIG. 26 is a vertical cross-sectional view of the core showing tenth embodiment of the present invention.

FIG. 26 shows tenth embodiment of the endoscope of the present invention. The endoscope of this embodiment has nearly the same basic structure as the endoscope of ninth embodiment. Therefore, the same reference numbers are given to the aforementioned components and their explanation is omitted.

In the endoscope of this embodiment, as shown in FIG. 26, a hole 530 is formed in the rear surface of the lens barrel 501. An endless groove 530a is formed in the inner wall of the hole 530. An adaptor's side electrode substrate 531 having nearly the same shape as the hole 530 is embedded in the hole 530. The adaptor's side electrode substrate 531 has a circular projection 531a on the periphery. The circular projection 531a fits into the groove 530a of the hole 530, whereby the adaptor's side electrode substrate 531 is fixed to the lens barrel 501. An adaptor's side electrode 509 is fixed to the rear surface of the adaptor's side electrode substrate 531.

Two through-holes 533 running in the axial direction of the lens adaptor 2 are formed in the lens barrel 501, substrate 503, and adaptor's side electrode substrate 531 provided in the adaptor housing 14. The through-holes 533 have an inner diameter larger than the inner diameter of the through-hole 510 of ninth embodiment.

The insulating plate 504 does not have a through-hole. Corresponding to the two through-holes 533, two electrodes 535 are provided on the rear surface of the insulating plate 504. Each electrode 535 is connected to the LED bare chips 18 bonded to the front surface of the insulating plate 504 via an electric line (not shown) embedded in the insulating plate 504.

Corresponding to the through-holes 533, two electrodes (not shown) are provided on the front surface of the adaptor's side electrode substrate 531. Each electrode is connected to the adaptor's side electrode 509 fixed to the rear surface of the adaptor's side electrode substrate 531 via an electric line (not shown) embedded in the adaptor's side electric substrate 531.

Connection pins 534 having terminals 534a and 534b at the ends are provided through the through-holes 533, respectively. The connection pins 534 are fixed to the inner surfaces of the through-holes 533 by, for example, bonding. The terminals 534a and 534b are electrically connected within the connection pin 534. The terminals 534a and 534b are retractably supported by the connection pin 534 and biased by a spring (not shown) built in the connection pin 534 in the opposite directions.

One terminal 534a of the connection pin 534 abuts the electrode 535 provided on the rear surface of the insulating plate 504 and the other terminal 534b of the connection pin 534 abuts the electrode provided on the front surface of the adaptor's side electrode substrate 531. In this way, the LED bare chips 18 and the adaptor's side electrode 509 are electrically connected.

The endoscope having the above structure is assembled as follow. First, the objective lens group 11 is installed in the lens barrel 501. The connection pins 534 are inserted in the through-holes 533s and fixed therein. After the connection pins 534 are fixed to the lens barrel 501 and substrate 503, the smaller diameter part 502 of the lens barrel 501 is inserted in the bores of the substrate 503 and insulating plate 504. The substrate 503 and insulating plate 504 are latched to the front surface of the lens barrel 501. When the insulating plate 504 is latched to the front surface of the lens barrel 501, one terminal 543a of the connection pin 534 abuts the electrode 535 provided on the rear surface of the insulating plate 504. Then, the adaptor's side electrode substrate 531 is pushed in the hole 530. When the adaptor's side electrode substrate 531 is pushed in the hole 530, the other terminal 534b of the connection pin 534 abuts the electrode provided on the front surface of the adaptor's side electrode substrate 531.

Then, the transmitting sealing plate 24 is placed in the adaptor housing 14 and, then, the lens barrel 501 is inserted. The outer periphery of the lens barrel 501 is bonded to the inner surface of the adaptor housing 14.

The endoscope of this embodiment significantly facilitates the placement and connection of electrodes compared to the prior art, remarkably improving assembly efficiency of the endoscope. Improving the assembly efficiency is very useful for down-sizing the insertion section 3 including the lens adaptor 2.

FIGS. 27 to 30 show eleventh embodiment of the endoscope of the present invention. The endoscope of this embodiment has nearly the same basic structure as the endoscope of ninth embodiment. Therefore, the same reference numbers are given to the aforementioned components and their explanation is omitted.

Figure 27:
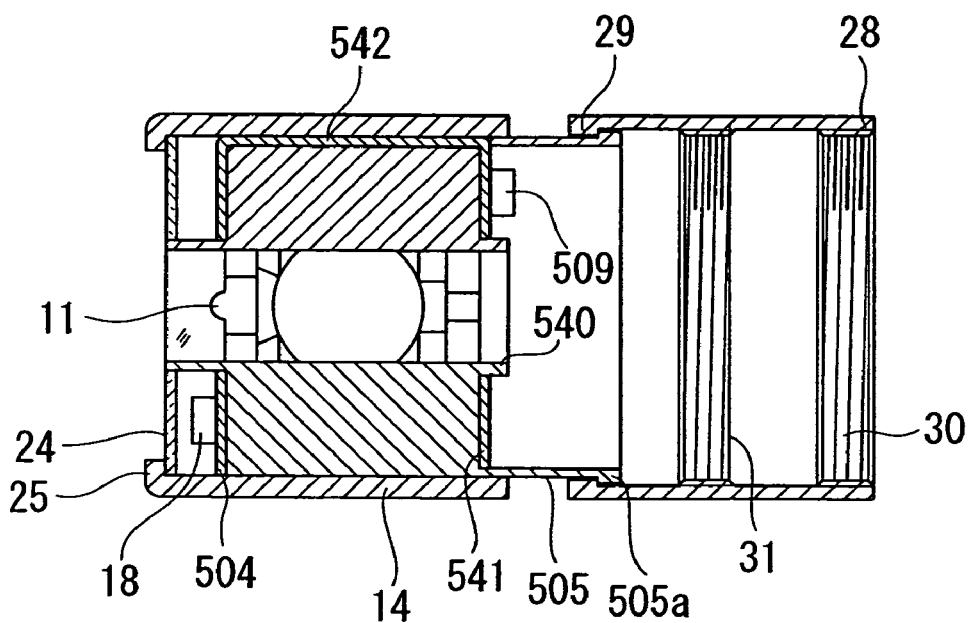
FIG. 27 is a vertical cross-sectional view of the core showing eleventh embodiment of the present invention.

In the endoscope of this embodiment, as shown in FIG. 27, the lens barrel 501 has on the back a smaller diameter part 540 protruding in the axial direction of the lens adaptor 2 and formed integrally therewith. An insulating plate 541 having a bored disc shape is fitted on the smaller diameter part 540. The insulating plate 541 is made of a flexible insulating material and an adaptor's side electrode 509 is fixed to the rear surface thereof. The outer diameter of the insulating plate 541 is nearly equal to the inner diameter of the adaptor housing 14. The inner diameter of the bore of the insulating plate 504 is nearly equal to the outer diameter of the smaller diameter part 540. The insulating plate 541 is fitted in an annular space formed between the adaptor housing 14 and the small diameter part 540.

The insulating plate 504 placed on the front surface of the lens barrel 501 and the insulating plate 541 placed on the rear surface of the lens barrel 501 are connected via a strip member 542 made of the same material. In other words, the insulating plate 504, insulating plate 541, and strip member 542 are all made of the same insulating material and integrally formed.

Figure 28:
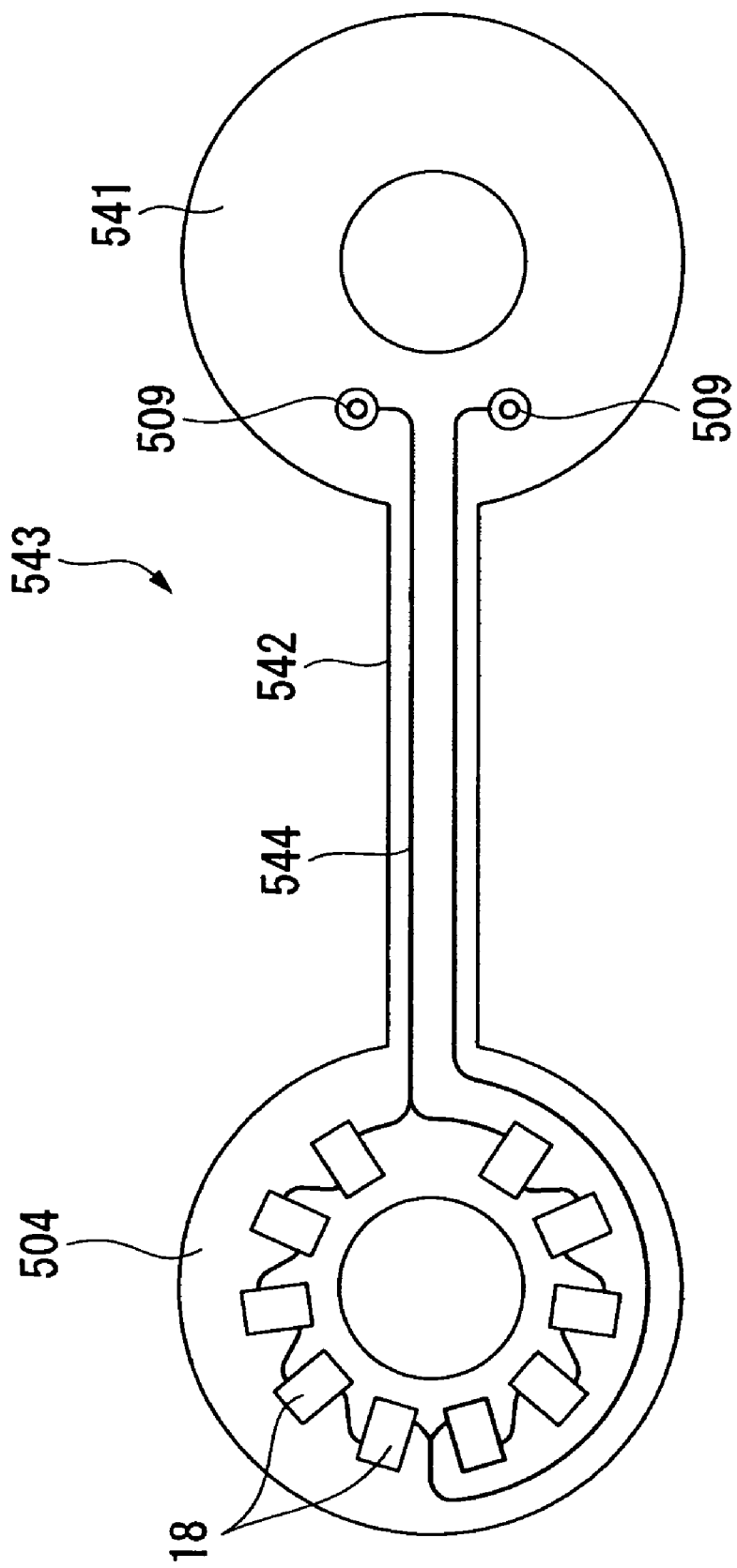
FIG. 28 is a plan view of an insulating plate provided in the endoscope of eleventh embodiment.
Figure 29:
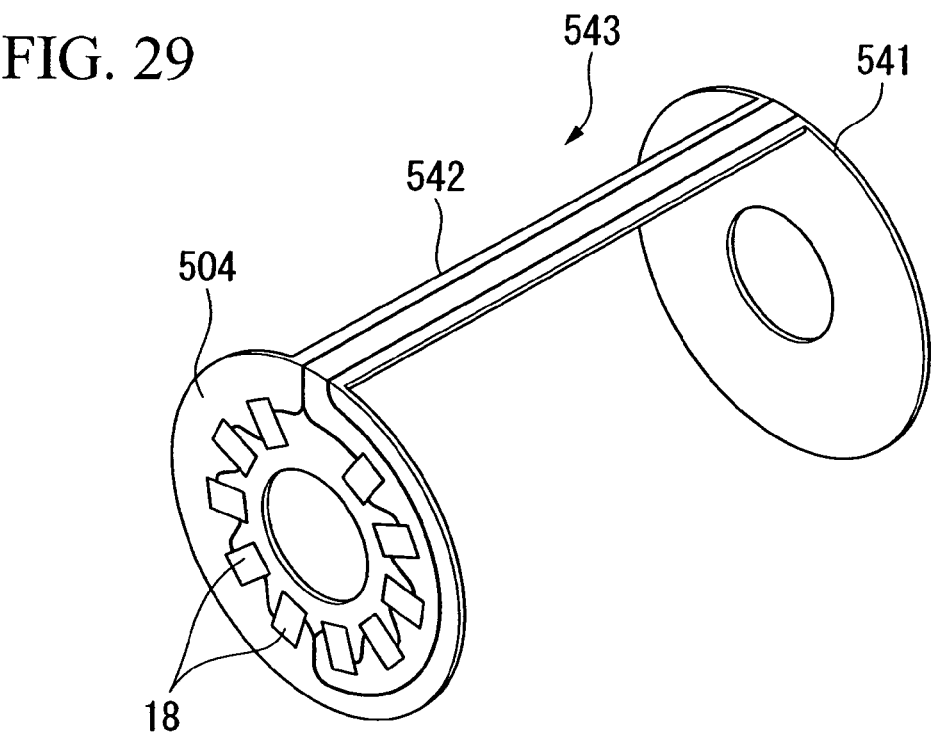
FIG. 29 is a perspective view showing the insulating plate provided in the endoscope of eleventh embodiment when it is folded.
Figure 30:
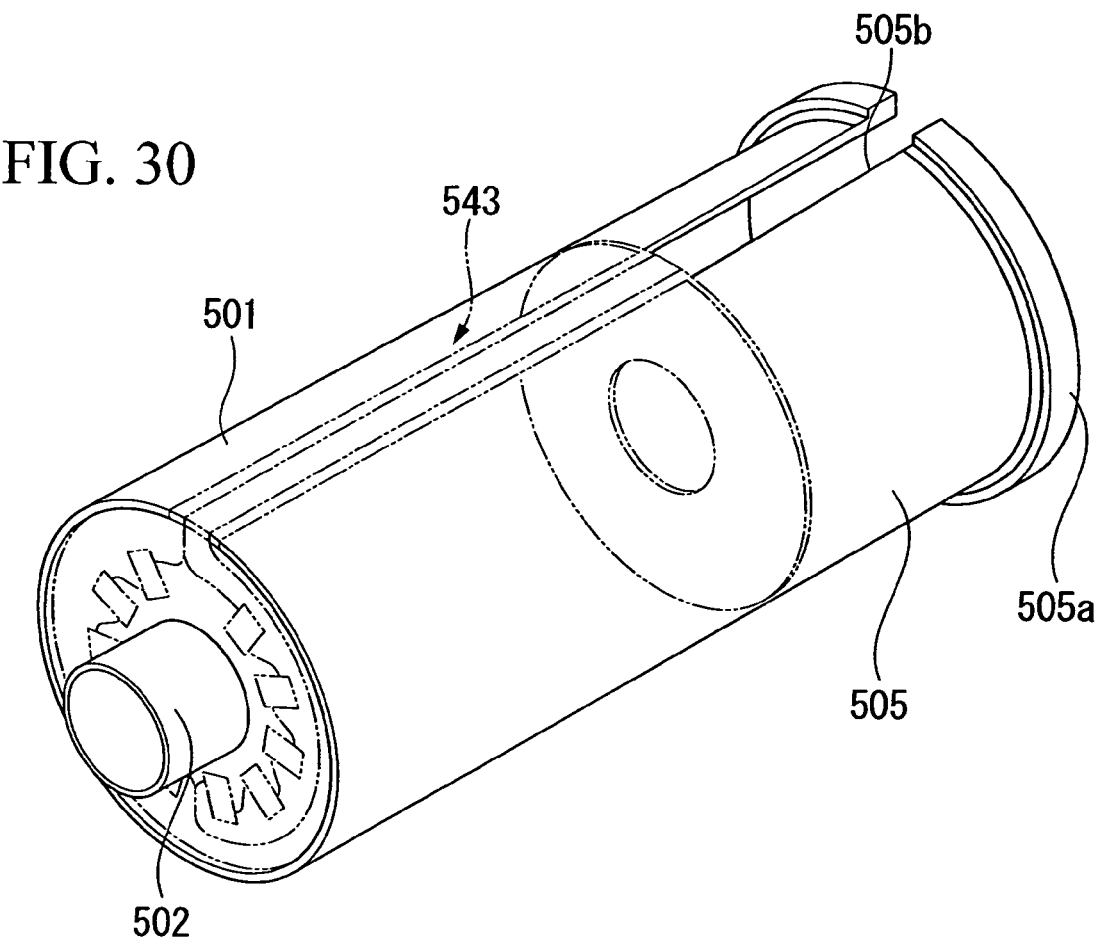
FIG. 30 is a perspective view of the lens barrel provided in the endoscope of eleventh embodiment.

As shown in FIG. 28, an insulating plate 543 consisting of the insulating plate 504, insulating plate 541, and strip member 542 originally has a flat form. Multiple LED bare chips 18 bonded to the insulating plate 504 are connected to the adaptor's side electrodes 509 fixed to the insulating plate 541 via electric lines 544 embedded in the insulating plate 504, insulating plate 541, and strip member 542. The insulating plate 543 is bent between the insulating plate 504 and the strip member 543 and between the insulating plate 541 and the strip member 542 when it is mounted on the lens barrel 501 as shown in FIG. 29.

A notch 505b is formed in the connection wall 505 of the lens barrel 501 to prevent interference with the insulating plate 543 mounted in the lens barrel 501.

The endoscope having the above structure is assembled as follows. First, the objective lens group 11 is installed in the lens barrel 501. Then, the smaller diameter part 540 on the rear surface of the lens barrel 501 is inserted in the bore of the insulating plate 542 while the strip member 542 is fitted in the notch 505b. The insulating plate 542 is latched to the rear surface of the lens barrel 501. The insulating plate 541 and strip member 542 are bent nearly at a right angle and the strip member 542 is laid along the exterior of the lens barrel 501. The insulating plate 504 and strip member 542 are bent nearly at a right angle. The smaller diameter part 502 of the lens barrel 501 is inserted in the bore of the insulating plate 504. The insulating plate 504 is latched to the front surface of the lane barrel 501.

Then, the transmitting sealing plate 24 is placed in the adaptor housing 14 and, then, the lens barrel 501 is inserted. The outer periphery of the lens barrel 501 is bonded to the inner surface of the adaptor housing 14.

The endoscope of this embodiment significantly facilitates the placement and connection of electrodes compared to the prior art, remarkably improving assembly efficiency of the endoscope. Improving the assembly efficiency is very useful for down-sizing the insertion section 3 including the lens adaptor 2.

FIGS. 31 to 34 show twelfth embodiment of the endoscope of the present invention. The same reference numbers are given to the components described in the above embodiments and their explanation is omitted.

Figure 31:
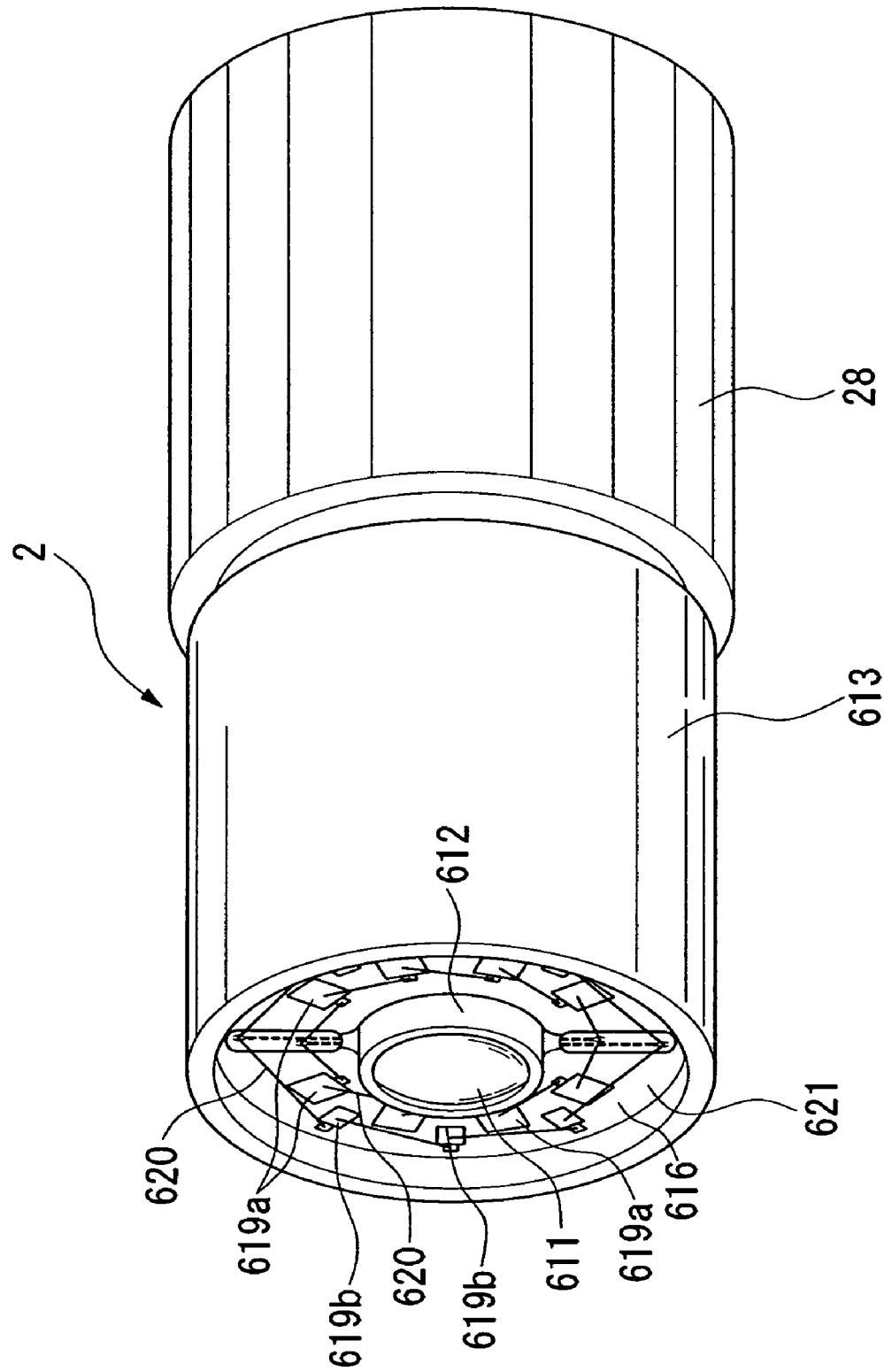
FIG. 31 is a perspective view of the core showing twelfth embodiment of the present invention.
Figure 32:
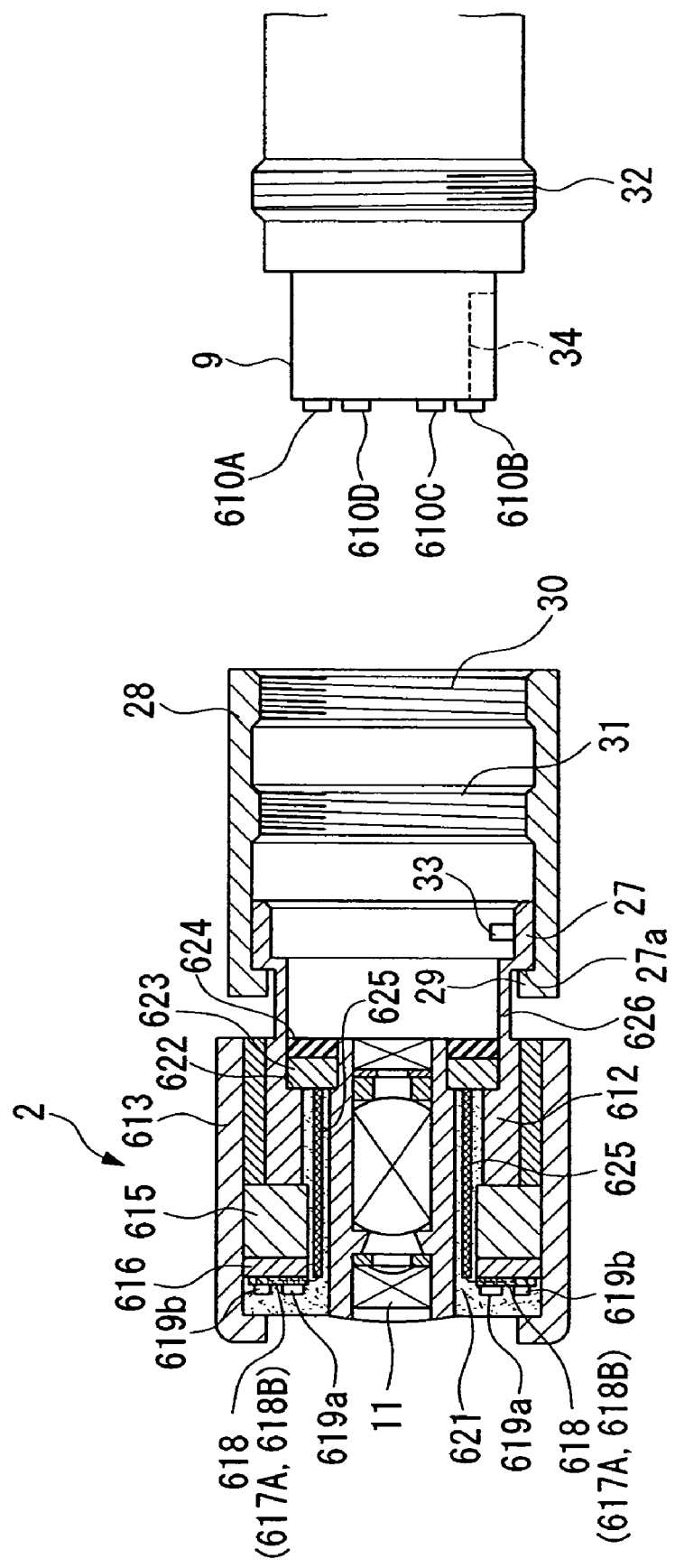
FIG. 32 is a vertical cross-sectional view of the core showing twelfth embodiment.

The lens adaptor 2 is a so-called straight view type. As shown in FIGS. 31 and 32, the objective lens group 11 that faces an object to be examined and forms an image of the object on the CCD of the coupling plug 9 is axially arranged in series. The objective lens group 11 is housed in a nearly cylindrical lens holder 612 and further housed in a cylindrical adaptor housing 613 together with an LED illumination unit 614 and spacer block 615, which are described later.

The LED illumination unit 614 includes a bored disc mounting base 616, electrode sheets 618, multiple LED bare chips 619a and 619b, and a fluorescent member 621.

Figure 33:
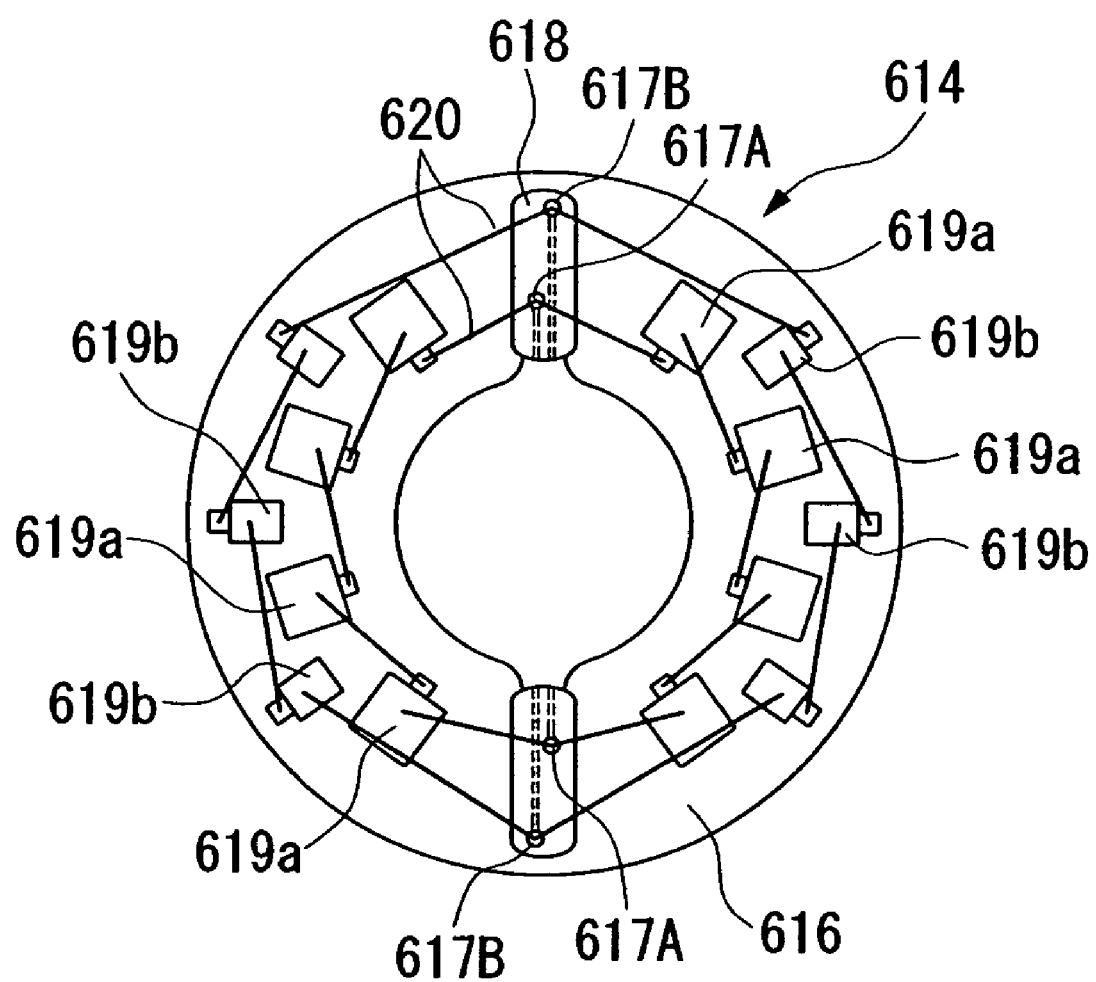
FIG. 33 is a front view of the core showing twelfth embodiment.

The mounting base 616 is made of a highly thermal conductive metal material such as aluminum. The electrode sheets 618 are bonded to the front surface of the mounting base 616 at the inner perimeter as shown in FIG. 33. The LED bare chips 619a and 619b are bonded to the front surface of the mounting base 616 together with the electrode sheets 618. The fluorescent member 621 is a transmitting sealing member covering the front surface of the LED bare chips 619a and 619b. Each electrode sheet 618 has two electrodes 617A and 617B on the upper surface of an insulating flexible plate. The LED bare chips 619a and 619b are connected to the electrodes 617A and 617B of the electrodes sheets 618 via wires 620 on the front surface of the mounting base 616.

The LED bare chips 619a and 619b have a nearly square shape in two different sizes. Specifically, eight larger LED bare chips 619a and six smaller LED bare chips 619b are used. A pair of electrode sheets 618 is symmetrically arranged about the center of the front surface of the mounting base 616. Two different-sizes of LED bare chips 619a and 619b are arranged in a circle, respectively, at circumferentially offset positions from each other on both sides of the electrode sheets 618.

The smaller LED bare chips 619b are arranged between adjacent ones of the larger LED bare chips 619a and slightly shifted outward in the radial direction from the center of the adjacent LED bare chips 619a. Four larger LED bare chips 619a are connected to the electrode metal 617A in series via wires 620 on each side of the electrode sheets 618. Three smaller LED bare chips 619b are similarly connected to the electrode metal 617B in series via wires (wire bonding) 620 on each side of the electrode sheets 618.

In this embodiment, the LED bare chips 619a and 619b are blue or purple LEDs. The fluorescent member 621 covering the front surface of these LED bare chips 619a and 619b is constituted by a fluorescent resin that can yield white light such as a YAG (yttrium/aluminum/garnet) fluorescent substance. The fluorescent member 621 is applied to cover the entire front surface of the mounting base 616 at a time after the electric sheets 618 and LED bare chips 619a and 619b are attached to the front surface of the mounting base 616 and the wires 620 are wire bonded.

On the other hand, an annular recess 622 is formed on the rear surface of the lens holder 612 as shown in FIG. 32. An electrode substrate 623 having a bored disc shape and a conductive rubber 624 are housed in the annular recess 622. Wires 625 are extended forward from the electrode substrate 623 and connected to the electrodes 517A and 6127B of the electrode sheets 618 on the front surface of the mounting base 616. The wires 625 are connected to not-shown electrodes on the electrode substrate 623 and these electrodes are pressed against the conductive rubber 624 behind them. The conductive rubber 624 is made of an insulating rubber material such as silicone rubber where a conductive material such as nickel particles and gold-plated metal particles is embedded in dots. Generally, it is called a dot-type anisotropic conductive rubber. When the elastic rubber material of the conductive rubber 624 having the above structure is pressed across the thickness, the conductive rubber 624 has increased conductivity where the density of the conductive material is increased as a result of compressive deformation and, therefore, becomes conductive through the thickness. However, because the rubber material is insulating, the conductive rubber 624 is still insulated in any directions (for example the circumferential direction) except for through the thickness.

The conductive rubber 624 is pressed by four electrodes 610A to 610D of the coupling plug 9 from behind when the lens adaptor 2 is connected as described later. Therefore, it becomes conductive at the parts pressed by the electrodes 610A to 610D and only the electrodes on the electrode substrate 623 and the coupling plug 9 at corresponding positions are electrically connected.

The lens holder 612 has at the rear end a connection wall 626 protruding from the adaptor housing 613 backward. The connection wall 626 is provided at the protruding edge with a connection wall 27 as a diametrically enlarged stepped part. The cylindrical connection ring 28 is fitted on the connection wall 27 in an axially and rotatably movable manner. The connection ring 28 has an inward stopper flange 29 integrally formed at one end, which abuts the stepped part 27a of the connection wall 27. A first female thread 30 and a second female thread 31 are formed on the inner periphery of the connection ring 28 at a predetermined axial interval.

On the other hand, the fixing male thread 32 is formed on the outer periphery of the coupling plug 9. The first and second female threads 30 and 31 of the connection ring 28 are screwed onto the male thread 32 in sequence, whereby the lens adaptor 2 can be coupled to the coupling plug 9. The connection ring 28 of the lens adaptor 2 is fitted on the front end of the coupling plug 9 and is rotated in a certain direction as it is, whereby the stopper flange 29 abuts the stepped part 27a of the connection wall 27 and restricts the axial movement of the connection ring 28. In this state, the male thread 32 of the coupling plug 9 is screwed into the first female thread 30 and, then, into the second female thread 31. Consequently, the terminals 610A to 610D protruding from the front end of the coupling plug 9 press the conductive rubber 624, therefore being electrically connected to the electrodes on the electrode substrate 623 via the conductive rubber 614. After the male thread 32 of the coupling plug 9 is screwed in the second female thread 31, it is disengaged from the first female thread 30. However, the first female thread 30 serves as a stopper to prevent the lens adaptor 2 from falling off in case the screw connection between the male thread 32 and second female thread 31 is loosened.

As shown in FIG. 32, a positioning projection 33 is provided on the inner periphery of the connection wall 27 of the lens adaptor 2 and a receiving groove 34 is provided on the outer periphery of the coupling plug 9. When the lens adaptor 2 and the coupling plug 9 are coupled, the positioning projection 34 and receiving groove 35 are engaged, whereby, their peripheral positions are precisely aligned.

FIG. 34 shows the electric wiring for the LED illumination unit 614 of this endoscope. In the aforementioned lens adaptor 2, two sets of LED wires 635a and 635b are provided corresponding to two different sizes of LED bare chips 619a and 619b. The LED wires 635a and 635b are connected to a power circuit 637 via separate, respective electric current control circuits 636a and 636b (for example fixed electric current circuits).

The endoscope of this embodiment has the structure described above in which multiple LEDs are attached to the mounting base 616 as elements 619a and 619b and sealed with the common fluorescent member 621 at the front. A combination of different sizes of LED bare chips 619a and 619b is attached to the mounting base 616. Therefore, many LEDs can be densely placed on a limited space on the front surface of the mounting base 616. More LEDs can be densely attached for the same mounting space of the mounting base 616 or a smaller mounting space is required for the same number of LEDs. Hence, this endoscope ensures a sufficient amount of light without enlarging the outer dimensions of the lens adaptor 2.

Particularly, in this embodiment, different sizes of LED bare chips 619a and 619b are arranged in a circle, respectively, at circumferentially offset positions from each other on the front surface of the circular mounting base 616. Therefore, nearly square LED bare chips, which are difficult to densely arrange, are densely arranged on the front surface of the mounting base 616 with efficiency.

In the endoscope of this embodiment, the separate electric current control circuits 636a and 636b are connected to the LED wiring lines 635a and 635b corresponding to the different sizes of LED bare chips 619a and 619b, respectively. Therefore, the different sizes of LED bare chips 619a and 619b are constantly supplied with proper electric current. With the separate electric current control circuits 626a and 636b being connected to the LED wires 635a and 635b as in this embodiment, for example, inconvenient changes in electric current or voltage through the LED bare chips 619b do not occur even though a replacement adaptor 2A having only one kind of LED bare chips 619b is installed as shown in FIG. 34.

In twelfth embodiment shown in FIGS. 31 to 34, the different sizes of LED bare chips 619a and 619b are arranged in a circle, respectively, on the front surface of the circular mounting base 616. A combination of different shapes of LED bare chips 719a and 719b can be used as in thirteenth embodiment shown in FIG. 35A. In thirteenth embodiment, nearly square LED bare chips 719a and triangular LED bare chips 719b are used. Pairs of two attached triangular LED bare chips 719b are arranged between adjacent ones of nearly square LED bare chips 719a. The pairs of triangular LED bare chips 719a are arranged with their vertices oriented diametrically inward.

Figure 35B:
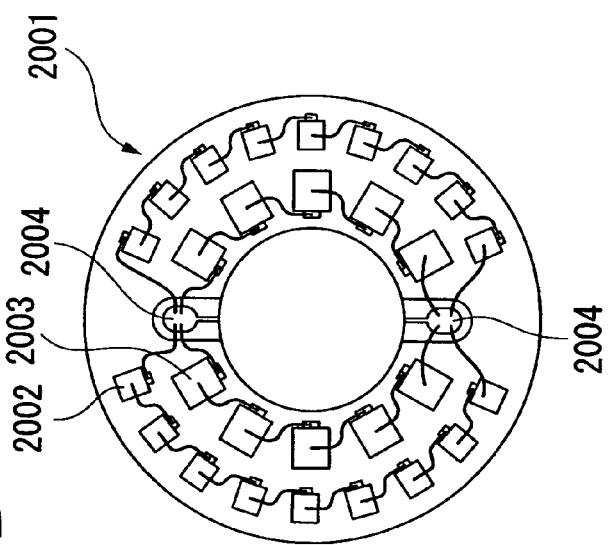
FIGS. 35B and 35C are schematic LED wiring diagrams provided in the endoscope of thirteenth embodiment.
Figure 35A:
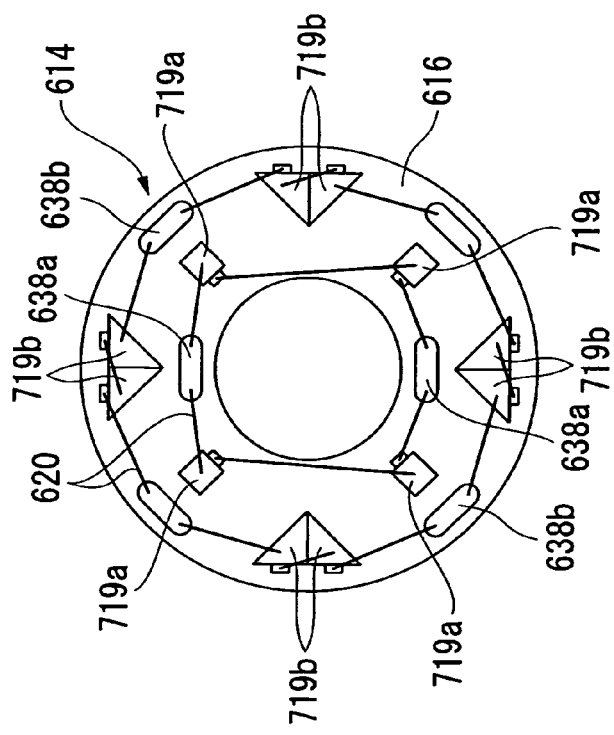
FIG. 35A is a front view of the core showing thirteenth embodiment of the present invention.

Electrodes 638a shown in FIG. 35A are provided for the nearly square LED bare chips 719a and electrodes 638b are provided for the triangular LED bare chips 719b.

Figure 35C:
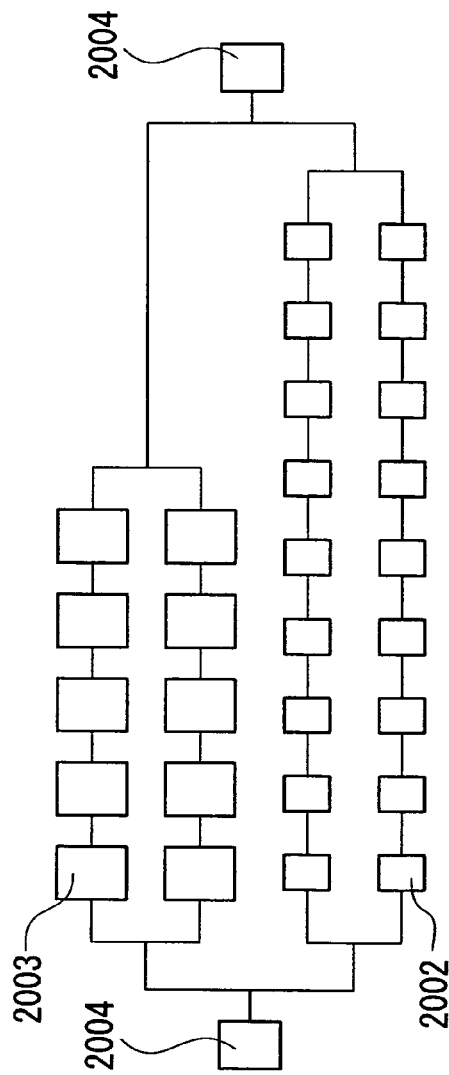

The endoscope of this embodiment basically yields the same efficacy as twelfth embodiment. However, because of the proper combination of different shapes of LED bare chips 718a and 718b on the mounting base 616, the LED bare chips 719a and 719b are densely arranged with further efficiency. As shown in FIG. 35, when the nearly square LED bare chips 719a are arranged in a circle, a sector shape space is created between adjacent LED bare chips. Idle spaces between the LED bare chips 719a and 719b can be further reduced by placing the triangular LED bare chips 719b between adjacent LED bare chips 719a as in this embodiment.

When different sizes of LED bare chips 2002 and 2003 are provided on the front surface of the mounting base 616, a larger number of the smaller LED bare chips 2002 are provided than the larger LED bare chips 2003. For example, five larger LED bare chips 2003 are connected in series and, similarly, five LED bare chips 2003 are connected in series; then, the two series are connected in parallel. On the other hand, nine smaller LED bare chips 2002 are connected in series and, similarly, nine LED bare chips 2003 are connected in series; then, the two series are connected in parallel. Further, the groups of the LED bare chips 2003 and the groups of the LED bare chips 2002 are connected in parallel and electrodes 2004 are provided at both ends of the connection lines. Using a larger number of the smaller LED bare chips 2002 than the larger LED bare chips 2003, the voltage between both ends of a group of the LED bare chips 2003 and the voltage between both ends of a group of the LED bare chips 2002 can be made approximately equal. Therefore, two electrodes 2004 can be provided.

Figure 36:
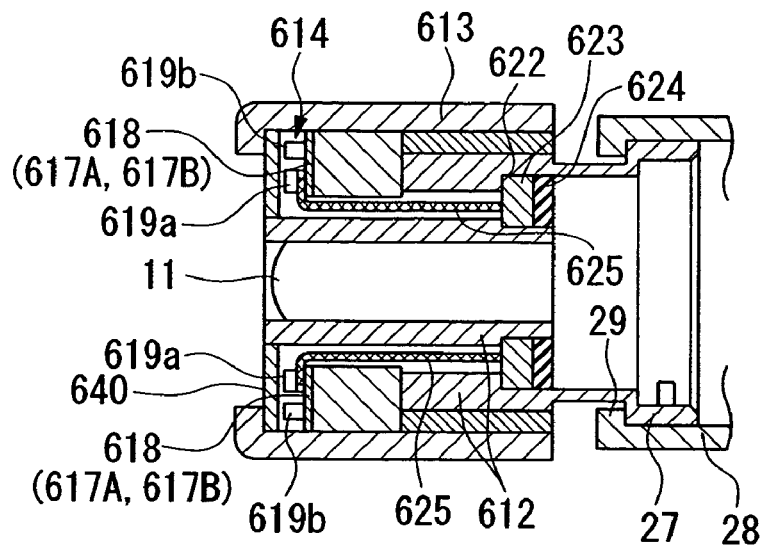
FIG. 36 is a vertical cross-sectional view of the core showing fourteenth embodiment of the present invention.

In the embodiment shown in FIGS. 31 to 34, the front surface of the mounting base 616 where different kinds of LED bare chips 619a and 619b are placed is covered with the common fluorescent member 621. When LED bare chips emitting white light are used or when non-white LED light is emitted as it is, a cover lens 640 can be provided as the transmitting sealing member on the front surface of the different kinds of LED bare chips 619a and 619b as in fourteenth embodiment shown in FIG. 36.

Figure 37:
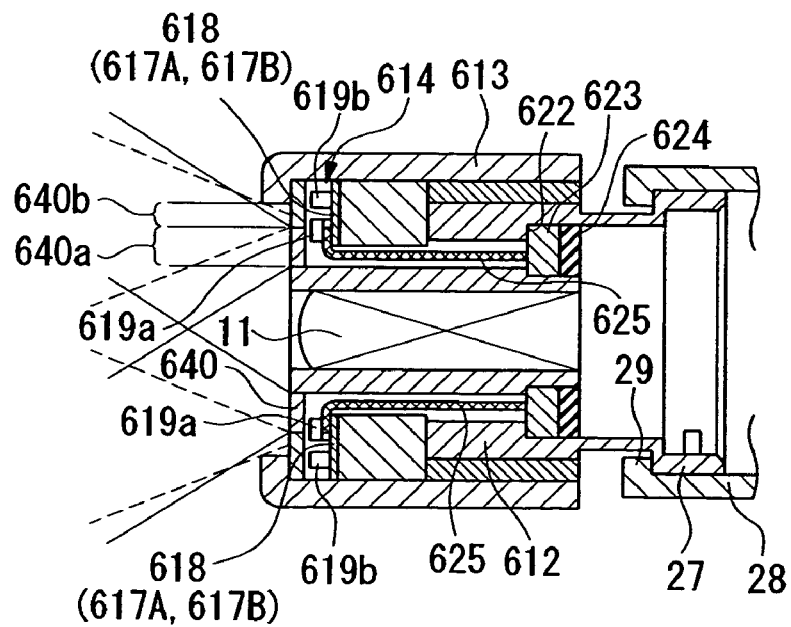
FIG. 37 is a vertical cross-sectional view of the core showing fifteenth embodiment of the present invention.

When the cover lens 640 is used to cover the front surface of the different kinds of LED bare chips 619a and 629b, the cover lens 640 can partly have different optical properties in part according to the nature of the LED bare chips 619a and 619b to cover at the front as in fifteenth embodiment shown in FIG. 37.

In the embodiment shown in FIG. 37, the cover lens 640 has different curvatures in the radially inner region 640a in front of the LED bare chips 619a and in the radially outer region 640b in front of the LED bare chips 619b. In this way, proper light distribution properties for the size and shape of the LED bare chips 619a and 619b can be obtained.

Figure 38:
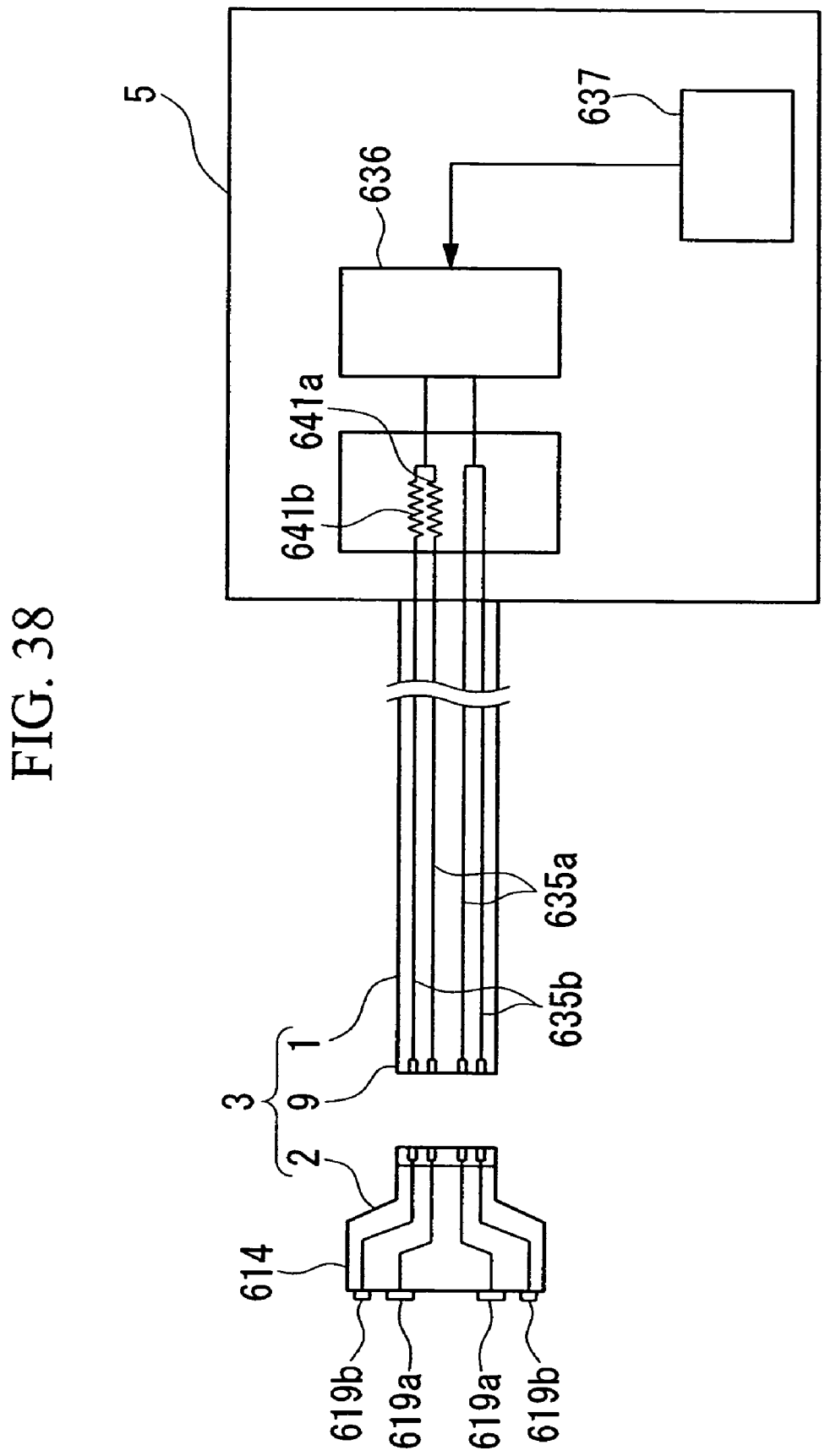
FIG. 38 is a schematic LED wiring diagram showing sixteenth embodiment of the present invention.

FIG. 38 shows sixteenth embodiment of the present invention. The endoscope of this embodiment has nearly the same basic structure as twelfth embodiment. However, it is different from twelfth embodiment in the wiring for the LED illumination unit 614. In this endoscope, LED wires 635a that connect the larger LED bare chips 619a and LED wires 635b that connect the smaller LED bare chips 619b are connected to a common electric current control circuit 36 in parallel. Electric current correction resistors 641a and 641b are interposed in the LED wires 635a and 635b in the apparatus body 5, respectively.

In this embodiment, the proper electric current correction resistors 641a and 641b are interposed in the LED wires 635a and 635b, respectively, whereby only one electric current control circuit 36 is used. This can simplify the apparatus circuit structure and reduce production cost. The electric current correction resistors 641a and 641b are not necessarily provided in the LED wires 635a and 635b and can be provided in any necessary LED wires.

Figure 39:
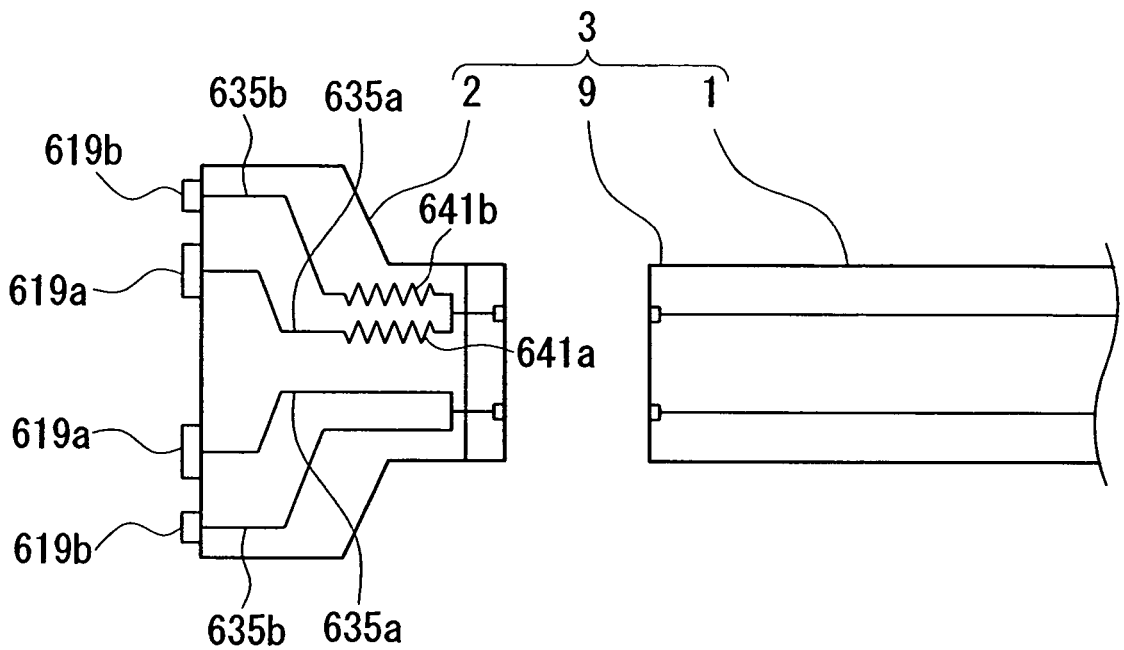
FIG. 39 is a schematic LED wiring diagram showing seventeenth embodiment of the present invention.

In sixteenth embodiment shown in FIG. 38, the electric current correction resistors 641a and 641b are interposed in the LED wires 635a and 635b in the apparatus body 5, respectively. However, the electric current correction resistors 641a and 641b can be interposed in the LED wires 535a and 635b in the lens adaptor 2, respectively, as in seventeenth embodiment shown in FIG. 39. In such a case, the LED wires 635a or 635b and the electric current correction resistor 641a or 641b of the LED bare chips 619a or 619b are installed in the lens adaptor 2 as a set. Therefore, another lens adaptor having a different LED bare chip specification can be easily replaced without adjusting circuits in the insertion section or in the apparatus body.

Figure 40:
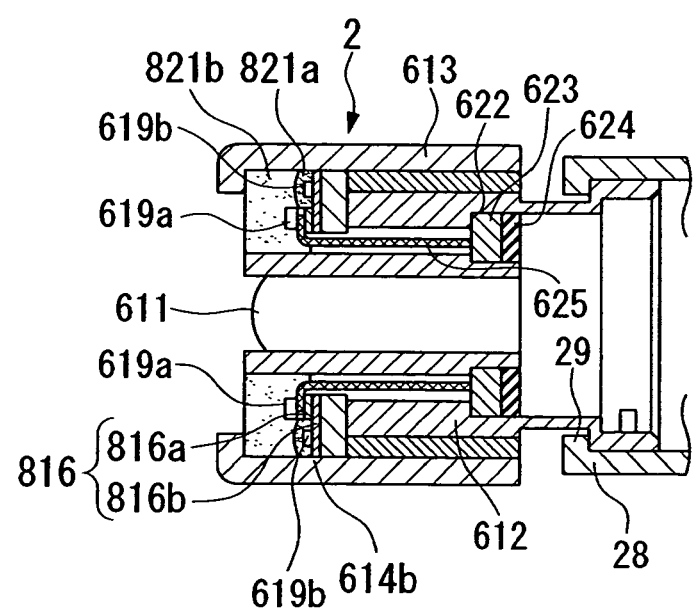
FIG. 40 is a vertical cross-sectional view of the core showing eighteenth embodiment of the present invention.
Figure 41A:
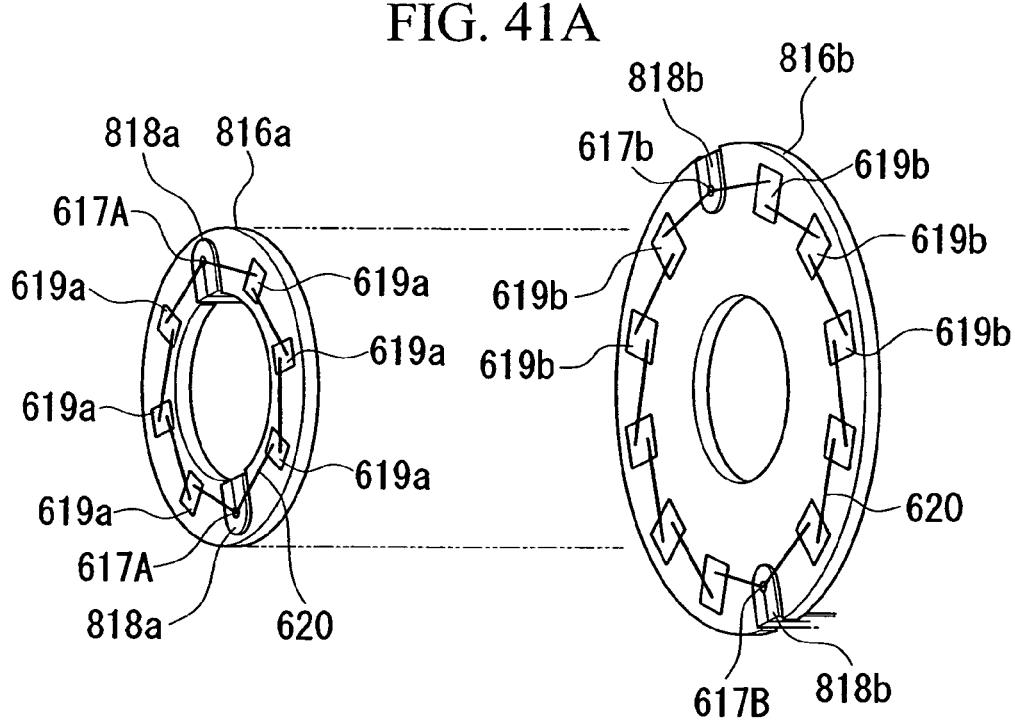
FIG. 41A is an exploded perspective view of the core of the endoscope of eighteenth embodiment.
Figure 41B:
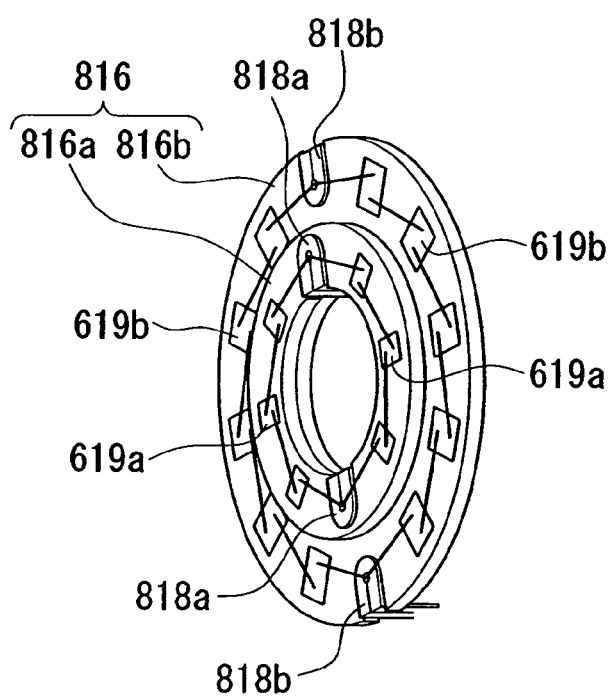
FIG. 41B is a perspective view of the endoscope of eighteenth embodiment after being assembled.

FIGS. 40, 41A and 41B show eighteenth embodiment of the present invention. The endoscope of this embodiment has nearly the same basic structure as twelfth embodiment. However, a mounting base 816 has a significantly different structure from that of twelfth embodiment.

The mounting base 816 of this embodiment consists of a first base plate 816a and a second base plate 816b fixed together and having a bored disc shape as shown in FIGS. 41A and 41B. Different sizes or shapes of LED bare chips 619a and 619b are attached to the base plates 816a and 816b. Specifically, the first base plate 816a is one size smaller than the second base plate 816b and has a pair of electrode sheets 818a and multiple LED bare chips 619a arranged in a circle on the front surface. The second base plate 816b has a pair of electrode sheets 818b and multiple LED bare chips 619b arranged in a circle on the front surface outside the area where the first base plate 816a is fixed. The LED bare chips 619a and 619b on the base plates 816a and 816b are connected to the electrodes 617A and 617B on the respective electrode sheets 818a and 818b via the wires 620. The first and second base plates 816a and 816b are fixed to each other by, for example, bonding, after the wires 620 of the LED bare chips 619a and 619b are completed.

The mounting base 816 formed as described above has a structure in which the first base plate 816a protrudes from the front surface of the second base plate 816b by one step at the center. The LED bare chips 619a are arranged in front of the LED bare chips 619b on the second base plate 816b. Fluorescent members 821a and 821b are applied to the front surface of the mounting base 816 assembled as described above as shown in FIG. 40 The front surface of all LED bare chips 619a and 619b are covered with the fluorescent members 821a and 821b. Specifically, one fluorescent member 821a is applied only to the front surface of the LED bare chips 619b on the second base plate 816b and the other fluorescent member 821b is applied to the front surface of the LED bare chips 619a on the first base plate 816a and the front surface of the fluorescent member 821a. Therefore, the fluorescent members 821a and 821b are both layered on the front surface of the LED bare chips 619b in the radially outer area of the mounting base 816 and only the other fluorescent member 821a is layered on the front surface of the LED bare chips 619a in the radially inner area.

In the endoscope of this embodiment, a combination of different sizes or shapes of LED bare chips 619a and 619b is arranged on the front surface of the mounting base 816 and their front surfaces are covered with the fluorescent members 821a and 821b as the transmitting sealing member. Similarly to twelfth embodiment, a basic efficacy of ensuring a sufficient amount of light can be achieved without enlarging the lens adaptor 2 (in diameter). In addition, in this embodiment, a single layer of the fluorescent member 821a is arranged on the front surface of the LED bare chips 619a and a double layer of fluorescent members 821a and 821b is arranged on the front surface of the other LED bare chips 619b. Therefore, the wavelength of light emitted forward can be changed according to the kinds of the LED bare chips 619a and 619b. For example, white light is emitted through the single layer of the fluorescent member 821a in front of the LED bare chips 619a while yellowish light is emitted through the double layer of the fluorescent members 821a and 821b in front of the LED bare chips 619b.

In the apparatus of this embodiment, the mounting base 816 is formed by two base plates 816a and 816b fixed together and having different diameters. Therefore, the base plates 816a and 816b can be fixed to each other after the LED bare chips 719a and 719b and electrode sheets 618 are attached thereto. Hence, parts assembly workability is improved.

Figure 42:
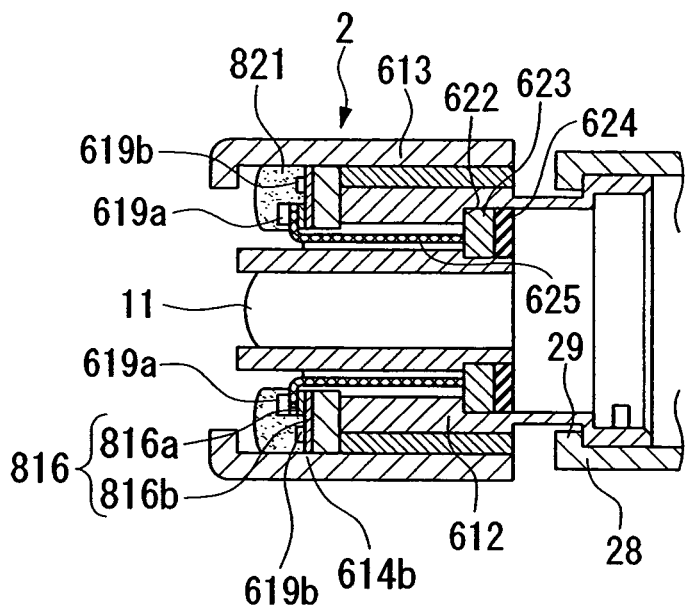
FIG. 42 is a cross-sectional view of the core showing nineteenth embodiment of the present invention.

In eighteenth embodiment, the fluorescent members having different properties are arranged on the front surface of different kinds of LED bare chips 719a and 719b (the single fluorescent member 821a is provided on the front surface of the LED bare chips 619a and the layered fluorescent members 821b and 821a are provided on the front surface of the LED bare chips 619b). A single fluorescent member 221 can be used to cover the front surfaces of the LED bare chips 619a and 619b differently in thickness as in nineteenth embodiment shown in FIG. 42. In the embodiment shown in FIG. 42, the outer LED bare chips 619b have larger output than the inner LED bare chips 619a. The fluorescent member 221 is thick on the front surface of the outer LED bare chips 619b and thin on the front surface of the inner LED bare chips 619a. Therefore, light emitted from the LED illumination unit 614 becomes nearly uniform white light over the entire front surface.

Figure 43:
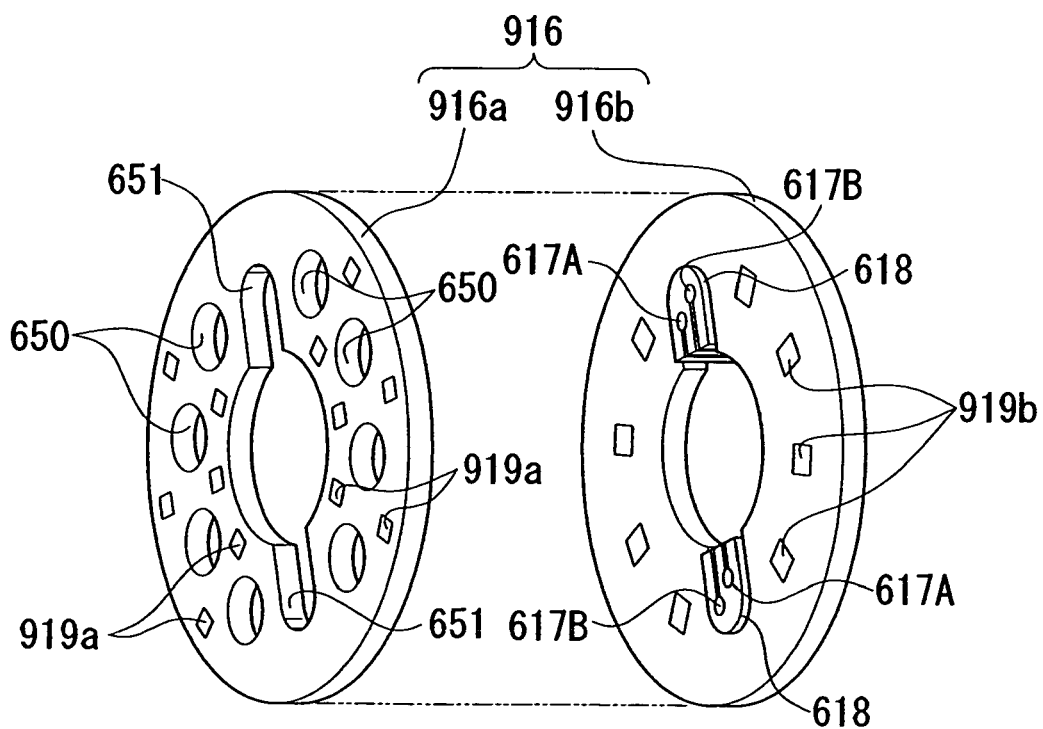
FIG. 43 is an exploded perspective view showing twentieth embodiment of the present invention.

FIG. 43 shows twentieth embodiment of the present invention. In this embodiment, the mounting base 316 is slightly modified from Embodiments 18 and 19. The mounting base 916 of this embodiment consists of two base plates 916a and 916b similarly fixed together. However, the two base plates 916a and 916b have nearly the same outer diameter. Multiple windows 650 are formed in a circle in a first base plate 916a arranged in front. Nearly square LED bare chips 319a are attached to the front surface of the first base plate 916a between adjacent windows 650 at radially inner positions and at radially outer positions. On the other hand, multiple nearly square LED bare chips 919b are attached to the front surface of a second base plate 916b arranged behind at the corresponding positions to the windows 650 in the first base plate 916a. A pair of electrode sheets 618 each having two electrodes 617A and 617B is also attached to the front surface of the second base plate 916b. In this embodiment, the LED bare chips 919a on the first base plate 916a are smaller than the LED bare chips 919b on the second base plate 916b.

One electrode 717B on the electrode sheet 618 is connected to the LED bare chips 919b on the second base plate 916b by wire bonding (the wiring is not shown). The other electrode 717A is similarly connected to the LED bare chips 919a via a notched groove 51 in the first base plate 916a when both base plates 916a and 916b are fixed together. Also in this embodiment, the transmitting sealing member such as a fluorescent member is provided on the front surface of the first base plate 916a to cover the front of all LED bare chips 919a and 919b.

In this embodiment, the different sizes of LED bare chips 919a and 919b are separately attached to the first base plate 916a and to the second base plate 916b. Therefore, the mounting and further dense arrangement of LED bare chips 919a and 919b can be advantageously facilitated.

Figure 44:
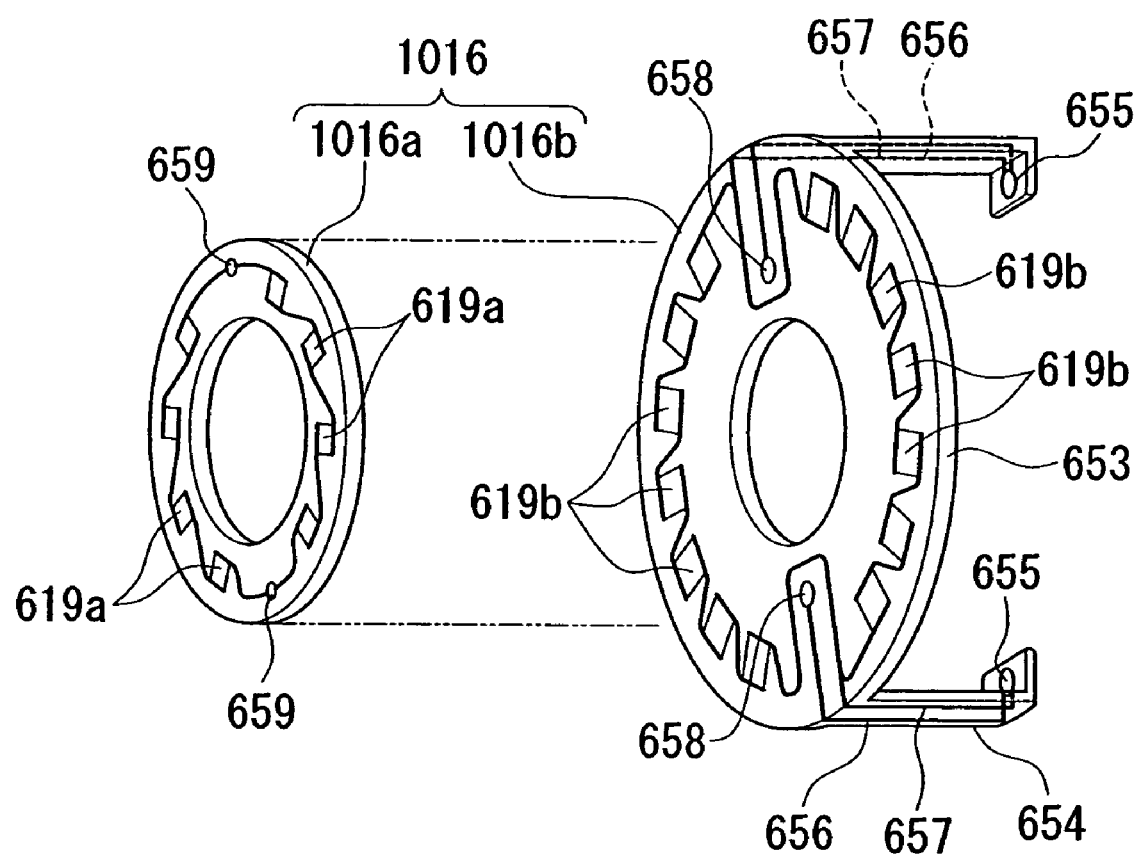
FIG. 44 is an exploded perspective view showing twenty-first embodiment of the present invention.

FIG. 44 shows twenty-first embodiment of the present invention. In this embodiment, as in eighteenth embodiment, a first, smaller outer diameter base plate 1016a is fixed on the front of a second base plate 1016b to form a mounting base 416. However, this embodiment is significantly different in that both base plates 1016a and 1016b consist of an insulating flexible plate. Specifically, the second base plate 1016b consisting of a flexible plate has a disc body 635, from the outer edge of which a pair of strips 654 is extended. Input electrodes 655 are provided at the tips of the strips 645. Wires 656 and 657 are embedded from the body 653 to the respective strips 654 and connected to input electrodes 655. The wires 656 of the second base plate 1016b are connected to the LED bare chips 619b bonded to the front surface of the body 653. The other wires 657 are connected to relay electrodes 658 provided on the front surface of the body 653.

On the other hand, the first base plate 1016a also consisting of a flexible plate has electrodes 659, which become conductive to the relay electrodes after the first base plate 1016a is fixed to the second base plate 1016b. The electrodes 659 are connected to the LED bare chips 619a bonded to the front surface of the first base plate 1016a.

The endoscope of this embodiment basically yields the same efficacy as eighteenth embodiment shown in FIGS. 40, 41A, and 41B. However, the base plates 1016a and 1016b can be easily mounted in a limited space and the wiring is facilitated because the base plates 1016a and 1016b are formed by flexible plates in which the wires 656 and 657, electrodes 655, and relay electrodes 658 are embedded.

Figure 45A:
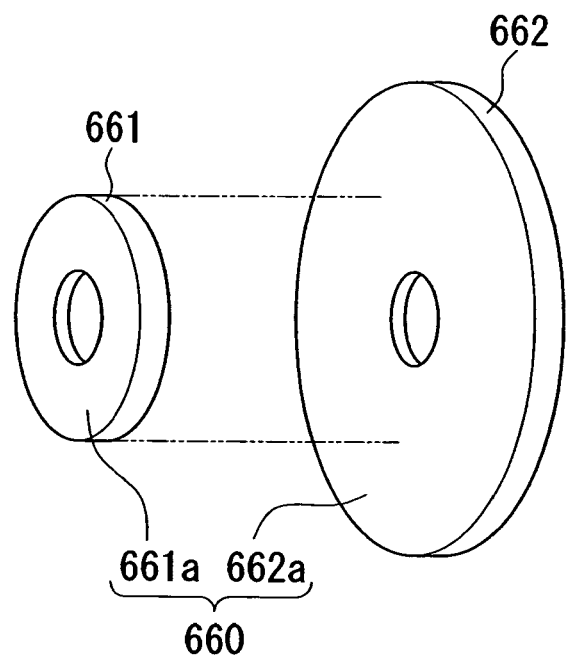
FIG. 45A is an exploded perspective view of the endoscope of twenty-second embodiment of the present invention.
Figure 45B:
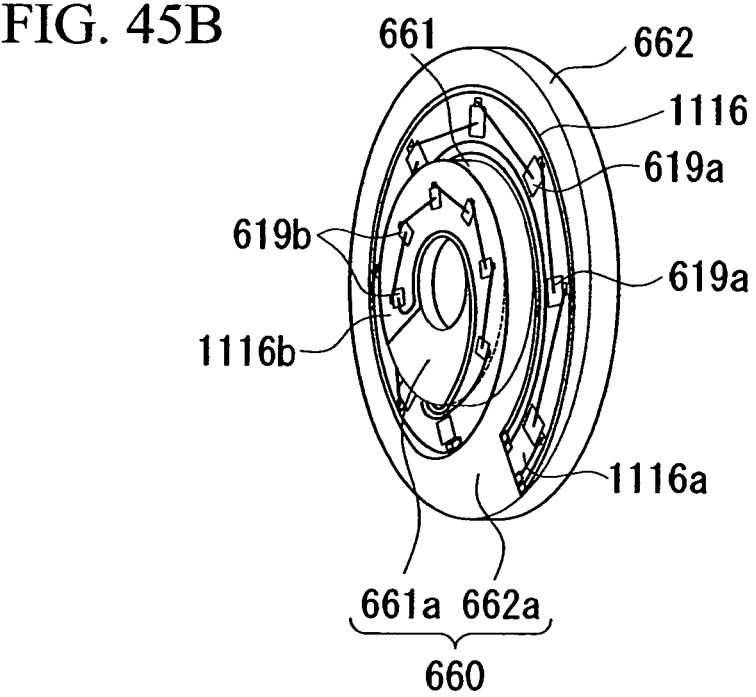
FIG. 45B is a perspective view of the completed endoscope of twenty-second embodiment.
Figure 46:
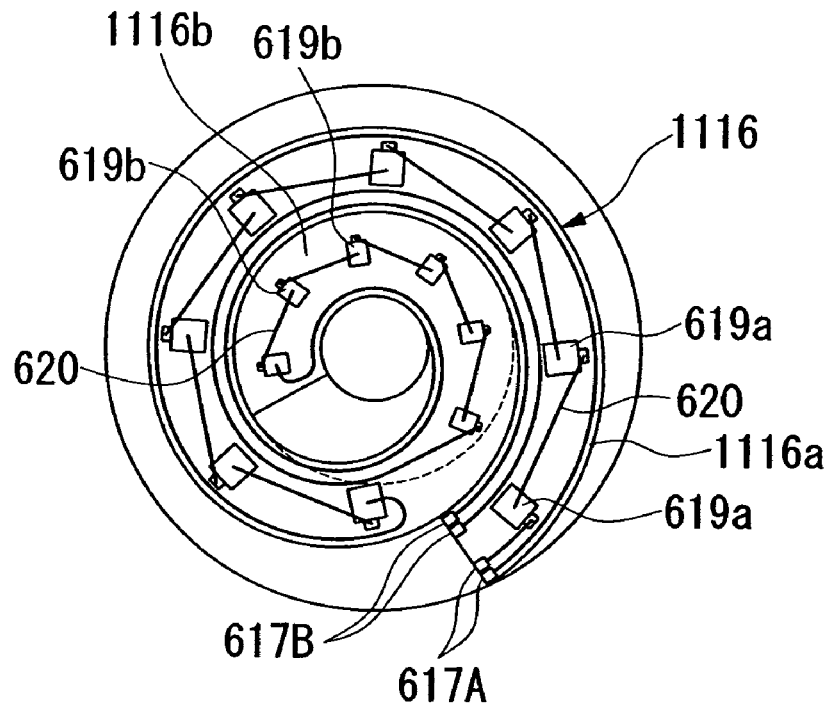
FIG. 46 is a plan view of the core showing twenty-second embodiment.

FIGS. 45A, 45B, and 46 show twenty-second embodiment of the present invention. A mounting base 1116 of this embodiment is formed by an insulating flexible plate as in twenty-first embodiment. However, the mounting base 1116 is different in that the flexible plate has a strip shape and is bonded to a mounting base supporting surface 660 having a step.

The mounting base 1116 is formed by a flexible plate having a continuous strip shape. It has a spiral shape toward the center under natural circumstances and a nearly disc shape as a whole in plan view.

Specifically, a radially outer region 1116a of the spiral of the mounting base 1116 is larger in strip width and an inner region 1116b is smaller in strip width. Larger, nearly square LED bare chips 619a are attached to the wider, outer region 1116a along the spiral and smaller, nearly rectangular LED bare chips 619b are attached to the narrower inner region 1116b along the spiral. The larger LED bare chips 619a and smaller LED bare chips 619b are connected to the electrodes 617A and 617B provided at the radially outer end of the strip, respectively, via the wires 620.

The mounting base supporting surface 660 is formed by a pair of metal disc members 661 and 662 as shown in FIG. 45A. The disc members 661 and 662 are fixed together before they are fixed to the insertion section. One disc member 661 has a smaller diameter than the other disc member 662. Being fixed together, the disc members 661 and 662 form the mounting base supporting surface 660 having a step in the front surface, whereby a first supporting surface 661a of one disc member 661 and a second supporting surface 662a of the other disc member 662 are formed.

The mounting base 1116 consists of a strip-shaped flexible plate is fixed to the mounting base supporting surface 660 of the disc members 661 and 662 as shown in FIG. 45B. The wider, radially outer region 1116a of the mounting base 1116 is bonded to the second supporting surface 662a of the larger diameter disc member 662. The narrower, radially inner region 1116b is bonded to the first supporting surface 661a of the smaller diameter disc member 661. The transition part up to the radially outer region 1116a is gently inclined and laid over the second supporting surface 662a. On the front surface of the mounting base 1116 attached to disc members 661 and 662 as described above, the fluorescent member or cover lens (not shown) is placed to cover the front surface of the LED bare chips 619a and 619b similarly to the other aforementioned embodiments.

In this embodiment, using the different sizes of LED bare chips 619a and 619b as in the other aforementioned embodiments, the LEDs can be densely arranged with efficiency. With the mounting base 1116 being made of a continuous strip of a flexible plate, efficient production and easy assembly can be advantageously realized. In this embodiment, the radially inner region 1116b of the mounting base 1116 is gently inclined and laid over the stepped part of the mounting base supporting surface 660. If the LED bare chips 619b are attached to the inclined part, the LED light distribution can be advantageously gradually changed.

Figure 47:
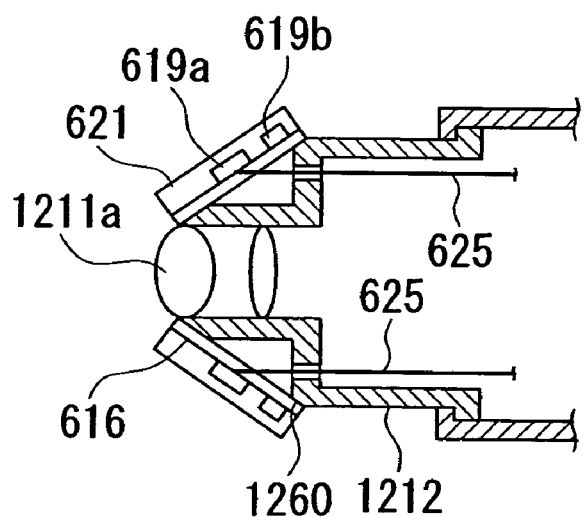
FIG. 47 is a vertical cross-sectional view of the core showing twenty-third embodiment of the present invention.
Figures 48A, 48B:
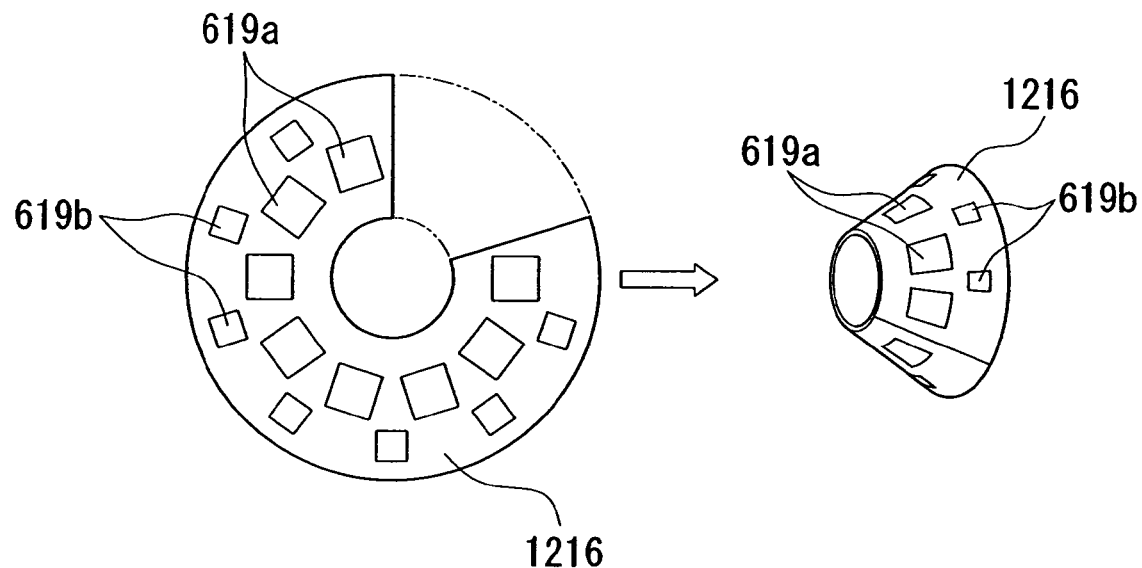
FIG. 48A is a developed plan view of the flexible plate of the endoscope of twenty-third embodiment before it is attached.
FIG. 48B is a perspective view of the endoscope of twenty-third embodiment after it is attached.

Twenty-third embodiment shown in FIGS. 47, 48A, and 48B is hereafter described. In the endoscope of this embodiment, a mounting base supporting surface 1260 having a truncated cone shape is provided at the distal end of a lens holder 1212 of the insertion section. A mounting base 1216 consisting of a flexible plate is attached to the mounting base supporting surface 1260. The mounting base 1216 is formed by cutting off a sector from a bored flexible disc member as shown in FIG. 48A, rolling it up into a truncated cone as shown in FIG. 48B, and bonding it to the mounting base supporting surface 1260. Multiple larger LED bare chips 619a and multiple smaller LED bare chips 619b are attached to the front surface of the mounting base 1216. As shown in FIG. 48A, the larger LED bare chips 619a are arranged in a circle and the smaller LED bare chips 619b are similarly arranged in a circle at circumferentially offset positions from the LED bare chips 619a. The LED bare chips 619a and 619b are connected to electrodes via wires, which are not shown in the figure.

On the tapered outer periphery of the mounting base 1216 attached to the lens holder 1212, the fluorescent member 621 or the transmitting sealing member is placed so as to cover the front surface of all the LED bare chips 619a and 619b. In this embodiment, an objective lens 1211a at the distal end is a wide-angle lens through which the front and surrounding area of the insertion section can be extensively observed.

This embodiment yields the same basic efficacy as the other aforementioned embodiments. In addition, with the mounting base 1216 consisting of a flexible plate being attached to the mounting base supporting surface 1260 having a truncated cone shape, the light emitted from the LED bare chips 619a and 619b can efficiently illuminate the front and surrounding area.

Figure 49:
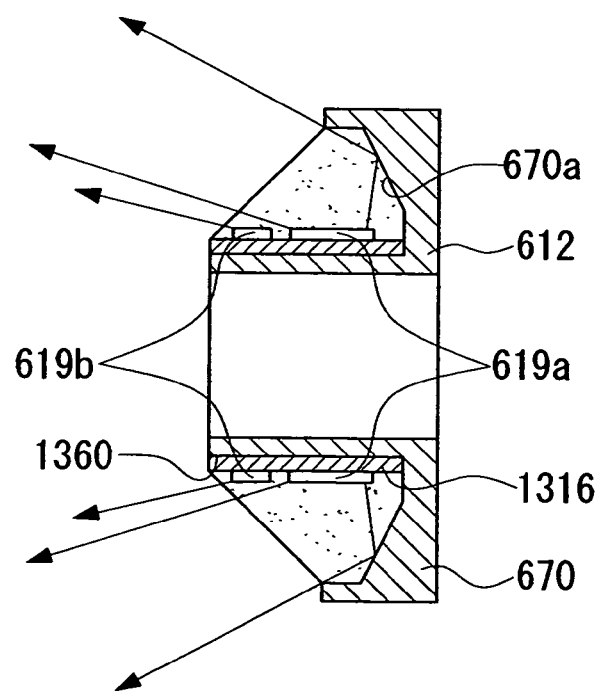
FIG. 49 is a cross-sectional view of the core showing twenty-fourth embodiment of the present invention.
Figure 50:
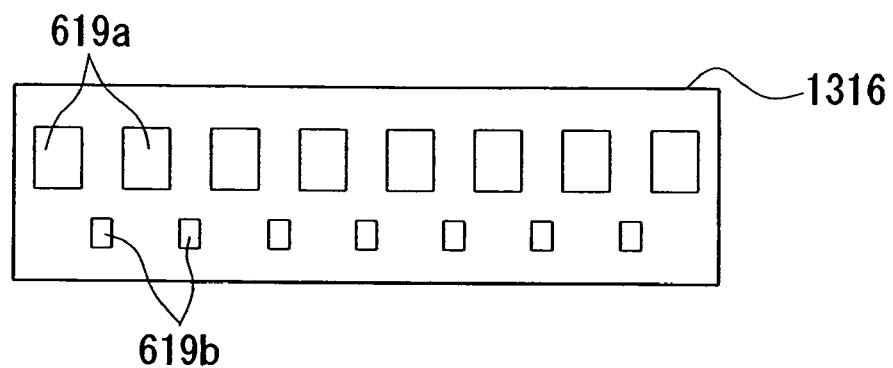
FIG. 50 is a developed plan view of the flexible plate showing twenty-fourth embodiment.
Figure 51:
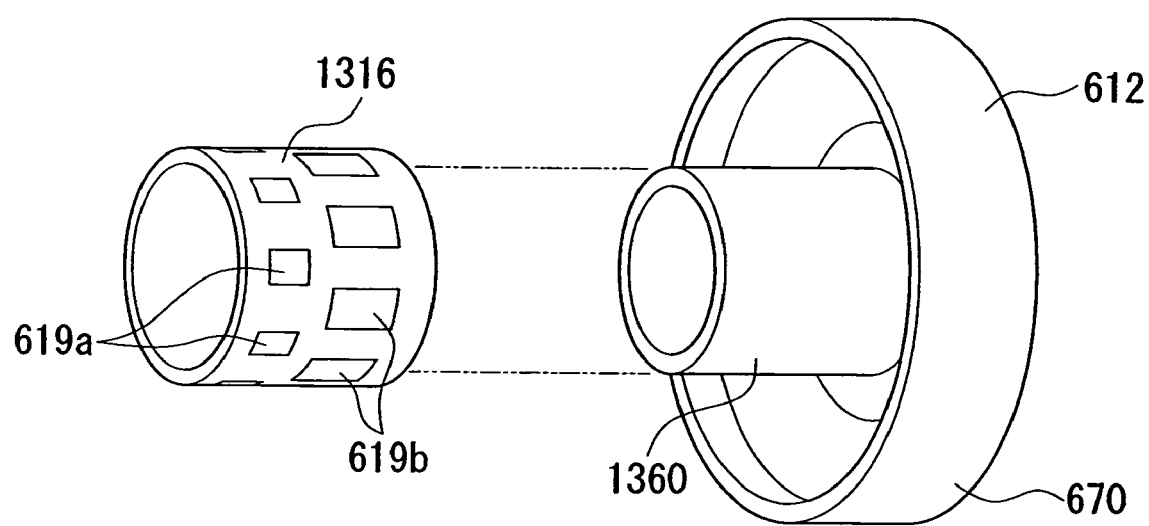
FIG. 51 is an exploded perspective view showing twenty-fourth embodiment.

FIGS. 49 to 51 show twenty-fourth embodiment of the present invention. In the endoscope of this embodiment, the lens holder 1212 has at the distal end a cylindrical outer surface that serves as a mounting base supporting surface 1360 and a mounting base 1316 consisting of a flexible plate 1316 is attached to the mounting base supporting surface 1360.

As shown in FIG. 50, the mounting base 1316 is formed by a strip of a flexible plate, to which the different sizes of LED bare chips 619a and LED bare chips 619b are attached in the longitudinal direction. The mounting base 1316 is rolled up into a cylinder shape and attached to the mounting base supporting surface 1360 as shown in FIG. 51. The different sizes of LED bare chips 619a and LED bare chips 619b are circumferentially offset from each other. The LED bare chips 619a and 619b are connected to electrodes via wires, which are again not shown in this embodiment.

The lens holder 1212 behind the mounting base supporting surface 1360 has at the back a reflecting wall 670 with a reflecting surface a on the front side. The reflecting surface 670a reflects light traveling backward and directs it forward among the light emitted from the LED bare chips 619a and 619b. Provided on the outer periphery of the mounting base 1316, the fluorescent member 621 or the transmitting sealing member is placed to cover the front surface of all LED bare chips 619a and 619b.

This embodiment also yields the basic efficacy in that the LEDs can be densely arranged. In addition, a sufficient amount of light is advantageously emitted to the surrounding area, particularly to the front surrounding area.

When the mounting base 1316 of this embodiment is formed by a flexible plate having a fixed width, an elongated flexible plate on which the same wiring pattern is repeated is previously formed and, then, an individual mounting base 1316 can be cut out from the flexible plate. The mounting base 1316 produced in this way can improve production efficiency and reduce production cost.

The endoscope of the present invention includes an adaptor detachably mounted on the distal end of an insertion section; illumination section provided in the adaptor; a mounting base provided in the adaptor and to the front of which the illumination section are attached; front electrode terminals provided at the front of the mounting base and connected to the illumination section; rear electrode terminals provided at the back of the mounting base, connected to the front electrode terminals, and abutting electrode terminals provided at the distal end of the insertion section when the adaptor is mounted on the distal end of the insertion section; and insulating plates where the front and rear electrode terminals are provided in such a manner that they are exposed from the surface and connection lines to connect the front and rear electrode terminals are embedded.

In the present invention, the insulating plates are attached to the mounting base by, for example, bonding, whereby a pair of electrode terminals connected to each other is easily placed at the front and back of the mounting base.

It is preferred in the endoscope of the present invention that the insulating plates be made of a flexible material.

In the present invention, when the insulating plate is attached to the mounting base, the insulating plate can be flexibly deformed according to the shape of the mounting base.

It is preferred in the endoscope of the present invention that an elastic member that supports the rear electrode terminals be provided between the rear electrode terminals and the mounting base.

In the present invention, when the adaptor is mounted on the distal end of the insertion section and the power terminals on the insertion section are pressed against the rear electrode terminals, the insulating plates are deformed and the elastic member that supports the rear electrode terminals is deformed. Consequently, the power terminals on the insertion section and the rear electrode terminals are reliably connected without causing damage to or deterioration of components.

It is preferred in the endoscope of the present invention that the part of the insulating plate where the rear electrode terminals are provided be raised as a projection and elastically deformable.

In the present invention, when the adaptor is mounted on the distal end of the insertion section and the power terminals on the insertion section are pressed against the rear electrode terminals, the protruding, raised part is flexibly and elastically deformed. Consequently, the power terminals on the insertion section and the rear electrode terminals are reliably connected without causing damage to or deterioration of components.

It is preferred in the endoscope of the present invention that a sensor be provided on the insulating plate. It is further preferred that the sensor be a temperature sensor, a pressure sensor, a humidity sensor, or a gravity direction detection sensor.

In the present invention, a sensor wiring can be built in the insulating plate.

The endoscope of the present invention includes an insertion section that is to be inserted in a lumen of an object to be examined; multiple illumination LED bare chips provided at the distal end of the insertion section; and a mounting base provided integrally with the insertion section, wherein the multiple LED bare chips include multiple kinds of LED bare chips that are different in shape or size; the multiple LED bare chips are attached to the mounting base; and the front surface of some of the multiple LED bare chips is covered with a transmitting sealing member.

In the present invention, LEDs are placed on the mounting base as elements. Therefore, a combination of different shapes or sizes of elements can be effectively arranged on the mounting base and the LEDs are densely placed in a limited space on the mounting base.

It is preferred in the endoscope of the present invention that among the multiple LED bare chips, one kind of LED bare chips be arranged between adjacent ones of a different kind of LED bare chips.

In the present invention, LED bare chips can be effectively arranged on the mounting base.

It is preferred in the endoscope of the present invention that the mounting base has a circular shape; one kind of LED bare chips among the multiple LED bare chips are arranged in a circle on the mounting base; and a different kind of LED bare chips are arranged in a circle at circumferentially offset positions from the one kind of LED base chips.

In the present invention, LED bare chips can be effectively arranged on a circular mounting base where it is difficult to arrange them densely.

It is preferred in the endoscope of the present invention that the transmitting sealing member be a fluorescent substance. It is preferred that the transmitting sealing member be partly changed in thickness according to the kind of LED bare chips to cover with the transmitting sealing member. It is further preferred that the transmitting sealing member be partly changed in material property according to the kind of LED bare chips to cover with the transmitting sealing member.

In the present invention, the wavelength of illumination light can be set according to the shape or size of LED bare chips.

It is preferred in the endoscope of the present invention that the transmitting sealing member be a cover lens. It is preferred that the transmitting sealing member be partly changed in optical property according to the kind of LED bare chips to cover with the transmitting sealing member.

In the present invention, a proper light distribution can be obtained according to the shape or size of LED bare chips.

It is preferred in the endoscope of the present invention that the mounting base consists of multiple base plates fixed together, each being provided with a different kind of LED bare chips.

In the present invention, the base plates are fixed together after LED bare chips are attached to each base plate. Therefore, components are easily mounted.

It is preferred in the endoscope of the present invention that the mounting base be a flexible insulating plate.

In the present invention, the mounting base can be flexibly deformed. Therefore, the mounting base can be easily mounted and freedom of design is also increased.

It is preferred in the endoscope of the present invention that the insertion section has a mounting base supporting surface having a truncated cone shape and the mounting base is attached to the mounting base supporting surface.

In the present invention, illumination light extends over the surrounding area in front of the insertion section.

It is preferred in the endoscope of the present invention that the insertion section has a mounting base supporting surface having a cylindrical shape and the mounting base is attached to the mounting base supporting surface.

In the present invention, light reliably illuminates the surrounding area of the insertion section.

It is preferred in the endoscope of the present invention that a reflecting surface be provided at the back of the mounting base.

In the present invention, light emitted by the LED bare chips is reflected forward by the reflecting surface. Therefore, the illumination rate to the front area of the inset part is increased.

It is preferred in the endoscope of the present invention that among multiple LED bare chips, the same kind of LED bare chips be connected by LED wires; and the LED wires be connected to separate, individual electric current control circuits.

In the present invention, an optimized electric current can be supplied to each LED wiring by an individual control circuit.

It is preferred in the endoscope of the present invention that among multiple LED bare chips, the same kind of LED bare chips be connected by LED wires; the LED wires be connected to a common electric current control circuit; and electric current correction resistors be provided to any LED wires.

In the present invention, one electric current control circuit can be shared by LED wires by simply providing electric current correction resistors to any LED wires. Therefore, production cost can be reduced.

It is preferred in the endoscope of the present invention that an adaptor detachably mounted on the distal end of the insertion section be further provided; and the multiple LED bare chips, mounting base, transmitting sealing member, LED wires, and electric current correction resistors be provided in the adaptor.

In the present invention, a replacement adaptor having a different LED bare chip specification can be used without any adjustments of circuits in the insertion section body and apparatus body.

In the present invention, the insulating plate can be attached to the mounting base by, for example, bonding, whereby a pair of electrode terminals connected to each other can be easily mounted at the front and back of the mounting base. Therefore, assembly efficiency of the adaptor can be improved and the adaptor can be down-sized.

In the endoscope of the present invention, a combination of different shapes or sizes of LED bare chips can be arranged on the mounting base and a common transmitting sealing member is used to cover the front surface of the multiple LED bare chips, whereby a sufficient number of LEDs can be densely arranged in a limited space on the mounting base. Therefore, the insertion section can be down-sized while ensuring a sufficient amount of light from LEDs.

Preferred embodiments of the present invention are described above. However, the present invention is not restricted to the aforementioned embodiments. Addition, elimination, replacement, and other modification of the components can be made without departing from the scope of the present invention. In the aforementioned embodiments, an endoscope that displays images captured by a CCD on image display means such as a liquid crystal panel is used for explanation. However, an endoscope with which an observer directly views images captured by a group of objective lenses through the ocular lens via an image guide such as an optical fiber is applicable.

What is claimed is:

1. An endoscope comprising:
   an adaptor detachably mounted on a distal end of an insertion section;
   a mounting base provided in said adaptor;
   an illumination section attached to the front of said mounting base;
   front electrode terminals provided at said front of said mounting base and connected to said illumination section;
   rear electrode terminals provided at the back of said mounting base, electrically connected to said front electrode terminals, and abutting electrode terminals provided at said distal end of said insertion section when said adaptor is mounted on said distal end of said insertion section; and
   insulating plates of which said front and rear electrode terminals are provided in such a manner that they are exposed from its surface and in which connection lines to connect said front and rear electrode terminals are embedded.

2. The endoscope according to claim 1, wherein said insulating plates are made of a flexible material.

3. The endoscope according to claim 1, wherein an elastic member that supports said rear electrode terminals is provided between said rear electrode terminals and said mounting base.

4. The endoscope according to claim 1, wherein the part of said insulating plate where said rear electrode terminals are provided is protruded and elastically deformable.

5. The endoscope according to claim 1, wherein a sensor is provided on said insulating plate.

6. The endoscope according to claim 5, wherein said sensor is a temperature sensor, a pressure sensor, a humidity sensor, or a gravity direction detection sensor.

7. An endoscope comprising:
   an adaptor detachably mounted on a distal end of an insertion section;
   a first flexible insulating plate provided in said adaptor;
   an illumination section attached to said first flexible insulating plate;
   adaptor's side electrode terminals provided at said first flexible insulating plate; and
   main body's side electrode terminals provided at a distal end of said insertion section wherein,
   a second flexible insulating plate is provided at said distal end of said insertion section, and
   said main body's side electrode terminals are provided at said second flexible insulating plate.

8. The endoscope according to claim 7, wherein said main body's side electrode terminals are formed integrally with said second flexible insulating plate.

9. The endoscope according to claim 7, wherein said main body's side electrode terminals are projection members fixed on a surface of said second flexible insulating plate.

10. The endoscope according to claim 7, wherein a power supply pad is provided on the surface of said second flexible insulating plate, and power supply lines are connected to said power supply pad.

11. The endoscope according to claim 7, wherein said second flexible insulating plate has through-holes, and power supply lines are connected to said power supply pad via electrodes provided inside said through-holes.

* * * * *